United States Patent [19]
Fernandez et al.

[11] Patent Number: 5,912,248

[45] Date of Patent: *Jun. 15, 1999

[54] EXCITATORY AMINO ACID RECEPTOR ANTAGONISTS

[75] Inventors: Carmen Dominguez Fernandez, Madrid, Spain; James Allen Monn; Matthew John Valli, both of Indianapolis, Ind.

[73] Assignee: Eli Lilly and Company, Indianapolis, Ind.

[*] Notice: This patent is subject to a terminal disclaimer.

[21] Appl. No.: 08/749,304

[22] Filed: Nov. 14, 1996

Related U.S. Application Data

[60] Provisional application No. 60/006,824, Nov. 16, 1995.

[51] Int. Cl.$^6$ .................. A01N 43/54; C07D 307/02; C07D 239/02; C07C 315/00

[52] U.S. Cl. .............. 514/256; 514/269; 514/471; 514/561; 514/562; 514/567; 544/335; 549/475; 549/476; 562/427; 562/430; 562/432; 562/457; 562/500

[58] Field of Search .................. 562/427, 430, 562/432, 457, 500, 501; 549/475, 496; 544/335; 514/256, 269, 471, 561, 562, 567

[56] References Cited

FOREIGN PATENT DOCUMENTS

| 696577 | 2/1996 | European Pat. Off. |
| WO 95/15940 | 6/1995 | WIPO |
| WO 96/04900 | 2/1996 | WIPO |
| WO 96/04901 | 2/1996 | WIPO |
| WO 96/05175 | 2/1996 | WIPO |
| WO 96/07405 | 3/1996 | WIPO |

OTHER PUBLICATIONS

D. Schoepp, et al., "Selective Inhibition of Forskolin–stimulated Cyclic AMP Formation in Rat Hippocampus by a Novel mGluR Agonist, 2R, 4R–4–aminopyrrolidine–2,4–dicarboxylate", *Neuropharmacology*, 34(8), 843–850 (1995).

D. Schoepp, et al., "Pharmacological and functional characteristics of metabotropic excitatory amino acid receptors", *TiPS*, 11(12), 508–515 (1990).

D. Schoepp, et al., "Metabotropic glutamate receptors in brain function and pathology", *TiPS*, 14, 13–20 (1993).

Chemical Abstract vol. 107 No. 217322, Rizzo et al, "A convenient preparation of 4 and 5–substituted cyclopentenones", 1987.

*Primary Examiner*—John Kight
*Assistant Examiner*—Raymond Covington
*Attorney, Agent, or Firm*—Martin A. Hay

[57] ABSTRACT

Compounds of the formula

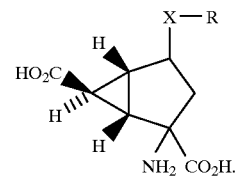

I in which X represents a bond, S, SO or $SO_2$; and R is as defined in the specification are useful as modulators of metabotropic glutamate receptor function.

10 Claims, No Drawings

EXCITATORY AMINO ACID RECEPTOR ANTAGONISTS

This application claims the benefit of U.S. Provisional Application No. 60/006,824 filed Nov. 16, 1995.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

The present invention provides a compound of formula

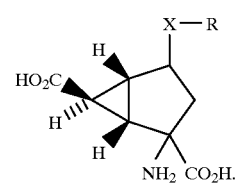

I in which X represents a bond, S, SO or $SO_2$; and R represents a (1-6C) alkyl group; a (2-6C)alkenyl group; a (2-6C)alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1-6C) alkyl, (2-6C)alkenyl or (2-6C)alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; or a non-toxic metabolically labile ester or amide thereof; or a pharmaceutically acceptable salt thereof.

It will be appreciated that the compounds of formula I contain at least five asymmetric carbon atoms; three being in the cyclopropane ring and two being in the cyclopentane ring. The present invention includes all stereoisomeric forms of the compounds of formula I, including each of the individual enantiomers and mixtures thereof.

Preferably the compounds of formula I have the configuration shown below

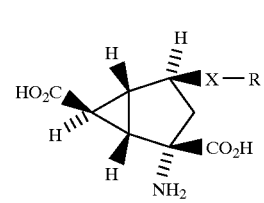

Ia

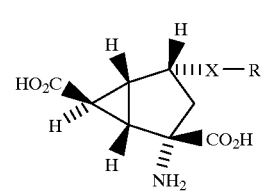

Ib

The configuration of formula Ib is most preferred.

As used herein, the term heteroaromatic group includes an aromatic 5-6 membered ring containing from one to four heteroatoms selected from oxygen, sulfur and nitrogen, and a bicyclic group consisting of a 5-6 membered ring containing from one to four heteroatoms selected from oxygen, sulfur and nitrogen fused with a benzene ring or a 5-6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzothiazolyl and indolyl.

The term aromatic group includes phenyl and a polycyclic aromatic carbocyclic ring such as naphthyl.

The term "optionally substituted", as used in the term "optionally substituted heteroaromatic or aromatic group", herein signifies that one or more substituents may be present, said substituents being selected from atoms and groups which, when present in the compound of formula I, do not prevent the compound of formula I from functioning as a modulator of metabotropic glutamate receptor functions.

Examples of atoms and groups which may be present in an optionally substituted heteroaromatic or aromatic group are amino, hydroxy, nitro, halogeno, (1-6C) alkyl, (1-6C) alkoxy, (1-6C)alkylthio, carboxy, (1-6C) alkoxycarbonyl, carbamoyl, (1-6C) alkanoylamino, (1-6C)alkylsulphonyl, (1-6C) alkylsulphonylamino, phenyl, phenoxy, phenylthio, phenylsulphonyl, phenylsulphonylamino, toluenesulphonylamino, and (1-6C)fluoroalkyl. Examples of particular values are amino, hydroxy, fluoro, chloro, bromo, iodo, methyl, methoxy, methylthio, carboxy, acetylamino, methanesulphonyl, nitro, acetyl, phenoxy, phenylthio, phenylsulphonyl, methanesulphonylamino and trifluoromethyl.

Examples of values for an optionally substituted aromatic group are 1-naphthyl, 2-naphthyl, phenyl, 2-biphenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4-dichlorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl, and 4-carboxyphenyl.

The term "non-aromatic carbocyclic group" includes a monocyclic group, for example a (3-10C)cycloalkyl group, such as cyclopropyl, cyclobutyl, cyclopentyl, cyclohexyl, cycloheptyl, cyclooctyl, cyclononyl or cyclodecyl, and a fused polycyclic group such as 1-adamantyl or 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl and bicyclo[3.3.1]non-1-yl,-2-yl,-3-yl or 9-yl.

The term "non-aromatic heterocyclic group" includes a 4 to 7 membered ring containing one or two heteroatoms selected from oxygen, sulphur and nitrogen, for example azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl.

The term "a non-aromatic monocyclic carbocyclic group fused with one or two monocyclic aromatic or heteroaromatic groups" includes a (3-10C)cycloalkyl group fused with a benzene ring or a an aromatic 5-6 membered ring containing from one to four heteroatoms selected from oxygen, sulfur and nitrogen, such as indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, -5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl.

The term "a non-aromatic monocyclic heterocyclic group fused with one or two monocyclic aromatic or heteroaromatic groups" includes a 4 to 7 membered ring containing one or two heteroatoms selected from oxygen, sulphur and nitrogen, fused with a benzene ring or a an aromatic 5-6 membered ring containing from one to four heteroatoms selected from oxygen, sulfur and nitrogen, such as 2,3-dihydrobenzopyran-2-yl, -3-yl or -4-yl, xanthen-9-yl, 1,2,3, 4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl.

Unless specified otherwise, the term "alkyl" means a straight chain or branched alkyl group. Examples of values for a (1-6C)alkyl group include (1-4C)alkyl such as methyl, ethyl, propyl, isopropyl, butyl and isobutyl.

The term (2-6C)alkenyl includes (2-4C)alkenyl such as allyl.

The term (2-6C)alkynyl includes (2-4C)alkynyl such as propynyl.

An example of a value for R when it represents an optionally substituted heteroaromatic group is 2-pyrimidyl.

When R represents an optionally substituted aromatic group, it preferably represents a 2-naphthyl group or a phenyl group which is unsubstituted or substituted by one or two substituents selected independently from halogen, (1-4C) alkyl and (1-4C) alkoxy.

Examples of values for R when it represents an optionally substituted aromatic group are 2-naphthyl, phenyl, 2-fluorophenyl, 3-fluorophenyl, 4-fluorophenyl, 3,4-difluorophenyl, pentafluorophenyl, 2-chlorophenyl, 3-chlorophenyl, 4-chlorophenyl, 3,4-dichlorophenyl, 2,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 3-trifluoromethylphenyl and 4-trifluoromethylphenyl.

Examples of values for R when it represents a substituted (1-6C)alkyl, (2-6C)alkenyl or (2-6C)alkynyl group are phenyl (1-4C)alkyl and diphenyl (1-4C)alkyl groups which are unsubstituted or substituted on phenyl by one or two of halogen, (1-4C)alkyl and (1-4C)alkoxy, for example benzyl, 2-phenylethyl, 2-phenylpropyl, and 2-thiophenylmethyl.

A preferred group of compounds of formula I is that in which R represents a (1-6C)alkyl group; a phenyl group which is unsubstituted or substituted by one or two substituents selected independently from halogen, (1-4C)alkyl and (1-4C)alkoxy; or a phenyl (1-4C)alkyl or diphenyl (1-4C) alkyl group which is unsubstituted or substituted on phenyl by one or two substituents selected from halogen, (1-4C) alkyl and (1-4C)alkoxy.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, a-hydroxybutyrate, glycolate, maleate, tartrate, methanesulfonate, propanesulfonate, naphthalene-1-sulfonate, naphthalene-2-sulfonate, mandelate, magnesium, tetramethylammonium, potassium, trimethylammonium, sodium, methylammonium, calcium, and the like salts.

Pharmaceutically acceptable metabolically labile ester and amide of compounds of formula I are ester or amide derivatives of compounds of formula I that are hydrolyzed in vivo to afford said compound of formula I and a pharmaceutically acceptable alcohol or amine. Examples of metabolically labile esters include esters formed with (1-6C) alkanols in which the alkanol moiety may be optionally substituted by a (1-8C) alkoxy group, for example methanol, ethanol, propanol and methoxyethanol. Example of metabolically labile amides include amides formed with amines such as methylamine.

According to another aspect, the present invention provides a process for the preparation of a compound of formula I which comprises (a) hydrolyzing a compound of formula

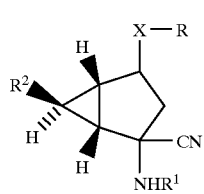

II in which $R^1$ represents a hydrogen atom or an acyl group and $R^2$ represents a carboxyl group or an esterified carboxyl group, or a salt thereof;

(b) hydrolyzing a compound of formula

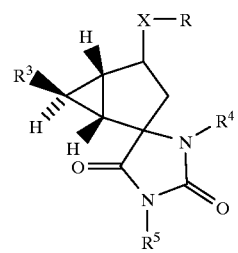

III in which $R^3$ represents a carboxyl group or an esterified carboxyl group, and $R^4$ and $R^5$ each independently represent a hydrogen atom, a (2-6C) alkanoyl group, a (1-4C) alkyl group, a (3-4C) alkenyl group or a phenyl (1-4C) alkyl group in which the phenyl is unsubstituted or substituted by halogen, (1-4C) alkyl or (1-4C) alkoxy, or a salt thereof; or (c) deprotecting a compound of formula

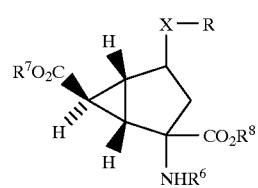

IV in which $R^6$ represents a hydrogen atom or a nitrogen protecting group and each of $R^7$ and $R^8$ independently represents a hydrogen atom or a carboxyl protecting group, or a salt thereof;

whereafter, if necessary and/or desired (i) resolving the compound of formula I;

(ii) converting the compound of formula I into a non-toxic metabolically labile ester or amide thereof; and/or;

(iii) converting the compound of formula I or a non-toxic metabolically labile ester or amide thereof into a pharmaceutically acceptable salt thereof.

The protection of carboxylic acid and amine groups is generally described in McOmie, Protecting Groups in Organic Chemistry, Plenum Press, New York, 1973, and Greene and Wuts, Protecting Groups in Organic Synthesis, 2nd. Ed., John Wiley & Sons, New York, 1991. Examples of carboxy protecting groups for $R^7$ and $R^8$ include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups for $R^6$ include acyl groups, such as groups of formula $R^{11}CO$ in which $R^{11}$ represents (1-6C) alkyl, (3-10C) cycloalkyl, phenyl(1-6C) alkyl, phenyl, (1-6C) alkoxy, phenyl(1-6C)alkoxy, or a (3-10C) cycloalkoxy, wherein a phenyl group may optionally be substituted by one or two substituents independently selected from amino, hydroxy, nitro, halogeno, (1-6C) alkyl, (1-6C) alkoxy, carboxy, (1-6C) alkoxycarbonyl, carbamoyl, (1-6C) alkanoylamino, (1-6C) alkylsulphonylamino, phenylsulphonylamino, toluenesulphonylamino, and (1-6C) fluoroalkyl.

Preferred values for $R^1$ are hydrogen and (2-6C)alkanoyl groups, such as acetyl.

Preferred values for $R^2$ and $R^3$ when they represent an esterified carboxyl group are (1-6C)alkoxycarbonyl groups such as ethoxycarbonyl.

Preferred values for $R^4$ and $R^5$ are hydrogen.

The compounds of formula II are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water and at a temperature in the range of from 50 to 200° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50 to 150° C.

The compounds of formula IV may be deprotected by a conventional method. Thus, an alkyl carboxyl protecting group may be removed by hydrolysis. The hydrolysis may conveniently be performed by heating the compound of formula IV in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range of from 10 to 300° C. An aralkyl carboxyl protecting group may conveniently be removed by hydrogenation. The hydrogenation may conveniently be effected by reacting the compound of formula IV with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0 to 100° C. An acyl, amine protecting group is also conveniently removed by hydrolysis, for example as described for the removal of an alkyl carboxyl protecting group.

The compounds of formula II may be prepared by reacting a compound of formula V

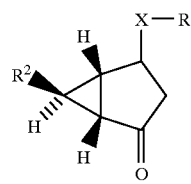

V with an alkali metal cyanide, such as lithium, sodium or potassium cyanide, and an ammonium halide, such as ammonium chloride. It has been found advantageous to perform the reaction in the presence of ultrasound. Thus, the ammonium halide is advantageously mixed with chromatography grade alumina in the presence of a suitable diluent such as acetonitrile. The mixture is then irradiated with ultrasound, whereafter the compound of formula V is added, and the mixture is again irradiated. The alkali metal cyanide is then added, followed by further irradiation with ultrasound.

The resultant mixture of diastereoisomeric aminonitriles may then be reacted with an acylating agent, such as acetyl chloride in the presence of a suitable base, for example an amine such as diisopropylethylamine and in the presence of a suitable solvent such as dichloromethane to afford a mixture of diastereomeric acylamino nitriles. The desired diastereoisomer may conveniently be separated from this mixture, for example by chromatography.

The compounds of formula III may be prepared by reacting a compound of formula V with an alkali metal cyanide, such as lithium, sodium or potassium cyanide, and ammonium carbonate in an aqueous alcohol, such as aqueous ethanol. Conveniently the reaction is performed at a temperature in the range of from 35 to 150° C. If desired, the compounds of formula III may then be alkylated or acylated for example using an appropriate compound of formula $R^4Cl$ and/or $R^5Cl$.

The compounds of formula V in which X represents S may be prepared by reacting a compound of formula VI

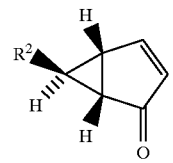

VI with a thiol of formula RSH. The reaction is preferably performed in the presence of a base, for example, a tertiary amine such as triethylamine. Suitable solvents for the reaction include ethers, such as tetrahydrofuran. The reaction is conveniently performed at a temperature in the range of from 0 to 100° C.

The compounds of formula V in which X represents a bond may be prepared by reacting a compound of formula VI with an organometallic reagent, such as a compound of formula RLi, RMgX or RZnX where X represents a halogen atom such as chlorine or bromine in the presence of a copper catalyst such as copper (I) iodide or copper (I) bromide $S(CH_3)_2$ adduct. Suitable solvents for the reaction include ethers such as diethyl ether, and tetrahydrofuran. The reaction is conveniently performed at a temperature in the range of from −40 to 10° C.

The compounds of formula VI may be prepared by reacting a compound of formula VII

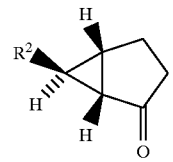

VII with iodotrimethyl silane in the presence of triethylamine to afford a silyl enol ether, and then reacting the silyl enol ether with palladium acetate.

The compounds of formula VII are known and may be prepared by reacting 2-cyclopenten-1-one with a carboxy protected (dimethyl sulfuranylidene) acetate. Suitable solvents for the reaction include aromatic hydrocarbons, such as toluene. The desired diastereomeric product may be isolated by chromatography.

The compounds of formula IV may be prepared by protecting a compound of formula I, for example by reaction with an alcohol such as ethanol in the presence of a dehydrating agent, such as thionyl chloride. Compounds of formula IV in which X represent S may be converted into the corresponding compounds of formula IV in which X represents SO or $SO_2$ by reaction with a peracid such as m-chloroperoxybenzoic acid.

The compounds of formula II, III and IV are believed to be novel, and are provided as further aspects of the invention.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester or amide thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester or amide thereof, or a pharmaceutically acceptable salt thereof.

Experiments were performed to demonstrate the ability of the formula I compounds to affect the excitatory amino acid receptors. The affinity for metabotropic glutamate receptors was demonstrated by the selective displacement of 1S,3R-ACPD-sensitive [$^3$H]glutamate binding to rat brain cell membranes. The binding of [$^3$H]glutamate was conducted with crude membranes of rat forebrain as described by Schoepp and True, *Neuroscience Lett.*, 145, 100–104 (1992) and Wright et al., J. Neurochemistry 63, 938–945, 1994. The compounds exemplified herein, except for the compound of Example 8, have all been found to have an $IC_{50}$ of less than 10 $\mu$M in this test. For example, the compound of Example 1 was found to have an $IC_{50}$ of 0.242 $\mu$M in this test. The compound of Example 8, which is not in the most preferred stereochemical configuration of formula Ib, was found to be essentially inactive.

Based on studies of receptor mediated changes in intracellar second messengers, metabotropic glutamate receptors are either coupled to enhanced phosphoinositide hydrolysis or decreases in forskolin-stimulated cAMP formation. Compounds of the present invention have been found to be modulators of metabotropic glutamate receptor function. More particularly, they have been found to be antagonists or agonists of metabotropic glutamate receptors, as measured by their effects on these second messenger systems. For example, compounds may be tested for ability to prevent inhibition of forskolin (30 $\mu$M)-stimulated cAMP formation by an mGluR agonist (1S,3R-ACPD, 20 $\mu$m) using slices of the rat hippocampus as described by D. D. Schoepp and B. G. Johnson, *Neurochemistry International* 22: 277–283 (1993) and human mGluR2 expressing non-neuronal cells (D. D. Schoepp et al., *Neuropharmacology*, 34, 843–850, 1995).

The compounds of the present invention are preferably formulated prior to administration. Therefore, another aspect of the present invention is a pharmaceutical formulation comprising a compound of formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 1

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight % |
| --- | --- |
| Active Ingredient | 0.25 |
| Ethanol | 29.75 |
| Propellant 22 | 70.00 |
| (Chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| Active Ingredient | 60 | mg |
| --- | --- | --- |
| Starch | 45 | mg |
| Microcrystalline cellulose | 35 | mg |
| Polyvinylpyrrolidone | 4 | mg |
| Sodium carboxymethyl starch | 4.5 | mg |
| Magnesium stearate | 0.5 | mg |
| Talc | 1 | mg |
| Total | 150 | mg |

The active ingredient, starch, and cellulose are passed through a No. 45 through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made follows:

| Active Ingredient | 80 | mg |
| --- | --- | --- |
| Starch | 59 | mg |
| Microcrystalline cellulose | 59 | mg |
| Magnesium stearate | 2 | mg |
| Total | 200 | mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 | mg |
| --- | --- | --- |
| Saturated fatty acid glycerides | 2,000 | mg |
| Total | 2,225 | mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| Active Ingredient | 50 | mg |
| --- | --- | --- |
| Sodium carboxymethyl cellulose | 50 | mg |
| Syrup | 1.25 | ml |
| Benzoic acid solution | 0.10 | ml |
| Flavor | q.v. |  |
| Color | q.v. |  |
| Purified water to total | 5 | ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| Active Ingredient | 100 | mg |
| --- | --- | --- |
| Mannitol | 100 | mg |
| 5 N Sodium hydroxide | 200 | ml |
| Purified water to total | 5 | ml |

The following Examples further illustrate the compounds of the present invention and the methods for their synthesis. Example 8 has been included to illustrate a method of synthesis only.

The following abbreviations are used in the following: EtOAc, ethyl acetate; THF, tetrahydrofuran; EtOH, ethanol;

TLC, thin layer chromatography; HPLC, high pressure liquid chromatography; m-CPBA, m-chloroperbenzoic acid; and FDMS, field desorption mass spectrometry.

PREPARATION 1

Carboethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88–90° C.

PREPARATION 2

(1SR,5RS,6SR) Ethyl 2-Oxobicyclo[3.1.0]hexane-6-carboxylate

A suspension of carboethoxymethyl dimethylsulfonium bromide (45.5 g, 198.6 mmol) in toluene (350 mL) was treated with 1,8-diazabicyclo[5.4.0]undec-7-ene (30.2 g, 198.4 mmol). The resulting mixture was stirred at room temperature. After one hour, the reaction mixture was treated with 2-cyclopenten-1-one (19.57 g, 238.4 mmol). After an additional 18 hours, the reaction mixture was added to a 1 N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g (68%) of the title compound. Melting point: 36–38° C.

FDMS: m/z=168 (M+).

Analysis calculated for $C_9H_{12}O_3$: C, 64.27; H, 7.19. Found: C, 64.54; H, 7.11.

EXAMPLE 1

1SR,2RS,4SR,5SR,6SR-2-Amino-4-(phenylthio)bicyclo[3.1.0]hexane-2,6-dicarboxylic acid (a) 1SR,5RS,6SR-Ethyl-2-oxobicyclo[3.1.0]hex-3-ene-6-carboxylate. Iodotrimethylsilane (75 g, 375 mmol) was added dropwise to a 0° C. solution of 1SR,5RS,6SR-ethyl-2-oxobicyclo[3.1.0]hexane-6-carboxylate (42 g, 250 mmol) and triethylamine (75 g, 750 mmol) in anhydrous $CH_2Cl_2$ (1000 mL). The resulting reaction mixture was allowed to warm to ambient temperature as it stirred overnight. The reaction mixture was washed with aqueous $NH_4Cl$ (3×) and brine, dried over $MgSO_4$, and concentrated in vacuo to yield the crude silyl enol ether. The product was reconstituted in anhydrous $CH_3CN$ (600 mL), treated in one portion with $Pd(OAc)_2$ (61.7 g, 275 mmol), and stirred at ambient temperature overnight. The reaction mixture was diluted with $Et_2O$ (600 mL) and filtered through a pad of Celite®. The filtrate was concentrated in vacuo to yield the crude product which was purified by HPLC (10% EtOAc/hexanes to 50% EtOAc/hexanes) affording 38.22 g (92%) of the title compound. mp=75–77° C. FDMS: M+=166. Anal. calcd. for $C_9H_{10}O_3$: C, 65.05; H, 6.07. Found: C, 65.11; H, 6.15.

(b) 1SR,4RS,5SR,6SR-Ethyl-2-oxo-4-(phenylthio)bicyclo[3.1.0]hexane-6-carboxylate. A solution of the product of step (a) (0.96 g, 5.8 mmol) in THF (100 mL) was treated with thiophenol (0.77 g, 6.7 mmol) followed by one drop of triethylamine. The reaction mixture was allowed to stir at room temperature until the reaction was judged complete by TLC. The reaction mixture was partitioned between EtOAc and 0.5 N HCl, the organic phase was collected, dried over $MgSO_4$, and concentrated to an oil which was purified by HPLC (10% EtOAc/hexane to 50% EtOAc/hexane) to yield 1.58 g (99%) of the title compound. FDMS: M++1= 277. Anal. calcd. for $C_{15}H_{16}O_3S.0.1$hexane: C, 65.75; H, 6.15. Found: C, 65.74; H, 6.20.

(c) 1SR,2RS,4SR,5SR,6SR-Ethyl-2-spiro-5'-hydantoin-4-(phenylthio)-bicyclo[3.1.0]hexane-6-carboxylate. The product of step (b) (5.5 g, 20 mmol) was combined with $(NH_4)_2CO_3$ (7.81 g, 100 mmol) and KCN (2.60 g, 40 mmol) in $H_2O$ (100 mL) and EtOH (100 mL) and the resulting mixture was warmed at 55° C. overnight. The product was filtered, washed with EtOH:$H_2O$ (50:50, 100 mL), and air dried to yield 5.0 g (72%) of the title compound. FDMS: M++1=347. Anal. calcd. for $C_{17}H_{18}N_2O_4S.H_2O$: C, 56.03; H, 5.53; N, 7.69; S, 8.80. Found: C, 56.13; H, 5.46; N, 7.73; S, 8.72.

(d) A suspension of the product of step (c) (2.9 g, 8.4 mmol) was heated with 5N NaOH (10 mL) at reflux for 72 h. The cooled aqueous solution was washed with EtOAc, then was acidified to a pH between 1 and 3 with HCl. The precipitate which formed was filtered, washed with $H_2O$ and 2-PrOH, and air dried to provide 1.43 g (58%) of the title compound. FDMS: M+=293. Anal. calcd. for $C_{14}H_{15}NO_4S.0.85$ NaCl: C, 49.02; H, 4.41; N, 4.08; S, 9.35. Found: C, 49.00; H, 4.57; N, 4.17; S, 9.24.

EXAMPLE 2

1SR,2RS,4SR,5SR,6SR-2-Amino-4-((3-chlorophenyl)thio)bicyclo[3.1.0]hexane-2,6-dicarboxylic acid (a) 1SR,4RS,5SR,6SR-Ethyl-2-oxo-4-((3-chlorophenyl)thio)bicyclo[3.1.0]hexane-6-carboxylate Following the method of Example 1(b), but employing 2.19 g (13.2 mmol) of the product of Example 1(a) and 1.91 g, (13.2 mmol) 3-chlorothiophenol, followed by trituration from hexane afforded 3.74 g (91%) of the title compound FDMS: M+=310, 312. Anal. Calcd. for $C_{15}H_{15}ClO_3S.0.1$hexane: C, 58.67; H, 5.18; S, 10.03. Found: C, 58.50; H, 4.97; S, 9.73.

(b) 1SR,2RS,4SR,5SR,6SR-Ethyl-2-spiro-5'-hydantoin-4-((3-chlorophenyl)thio)bicyclo[3.1.0]hexane-6-carboxylate Following the method of Example 1(c), but employing the product of step (a) (3.7 g, 11.7 mmol), $(NH_4)_2CO_3$ (4.5 g, 57.9 mmol) and KCN (1.5 g, 23.2 mmol), followed by filtering the product and recrystallization from EtOH afforded 0.3 g (7%) of the title compound. mp=256–258° C. FDMS: M+=380. Anal. calcd. for $C_{17}H_{17}ClN_2O_4S.EtOH$: C, 53.45; H, 5.43; Cl, 8.30; N, 6.56; S, 7.51. Found: C, 53.65; H, 5.28; Cl, 8.48; N, 6.35; S, 7.51.

(c) Following the method of Example 1(d), but employing the product of step (b) (0.29 g, 0.76 mmol) and 2N NaOH (20 mL) at reflux for 16 hours, work up afforded 0.20 g (80%) of the title compound. FDMS: M+=327 and 329. Anal. calcd. for $C_{14}H_{14}ClNO_4S$: C, 51.30; H, 4.31; N, 4.27; S, 9.78. Found: C, 51.49; H, 4.45; N, 4.07; S, 9.61.

EXAMPLE 3

1SR,2RS,4SR,5SR,6SR-2-Amino-4-((2-chlorophenyl)thio)bicyclo[3.1.0]hexane-2,6-dicarboxylic acid (a) 1SR,4RS,5SR,6SR-Ethyl-2-oxo-4-((2-chlorophenyl)thio)bicyclo[3.1.0]hexane-6-carboxylate Following the method of Example 1(b), but employing 2.19 g (13.2 mmol)

of the product of Example 1(a) and 1.91 g, (13.2 mmol) 2-chlorothiophenol, followed by trituration from hexane afforded 3.78 g (92%) of the title compound. FDMS: $M^+$=310, 312. Anal. Calcd. for $C_{15}H_{15}ClO_3S \cdot 0.1$ hexane: C, 58.67; H, 5.18; S, 10.03. Found: C, 58.28; H, 4.96; S, 9.81.

(b) 1SR,2RS,4SR,5SR,6SR-Ethyl-2-spiro-5'-hydantoin-4-((2-chlorophenyl)thio)-bicyclo[3.1.0]hexane-6-carboxylate Following the method of Example 1(c), but employing the product of step (a) (3.7 g, 11.7 mmol), $(NH_4)_2CO_3$ (4.5 g, 57.9 mmol) and KCN (1.5 g, 23.2 mmol), followed by filtration of the product and recrystallization from EtOH yielded 1.6 g (36%) of the title compound. mp=211–213° C. FDMS: $M^+$=380. Anal. calcd. for $C_{17}H_{17}ClN_2O_4S \cdot EtOH$ C, 53.45; H, 5.43; N, 6.56; S, 7.51. Found: C, 53.05; H, 5.25; N, 6.60; S, 7.26.

(c) Following the method of Example 1(d), but employing the product of step (b) (0.51 g, 1.3 mmol) and 2N NaOH (15 mL) at reflux for 48 hours, work up afforded 0.30 g (70%) of the title compound. mp>250° C. FDMS: $M^+$=327 and 329. Anal. calcd. for $C_{14}H_{14}ClNO_4S \cdot 0.65\ H_2O$: C, 49.38; H, 4.83; N, 4.11; S, 9.42. Found: C, 49.29; H, 4.44; N, 3.86; S, 9.31.

EXAMPLE 4

1SR,2RS,4SR,5SR,6SR-2-Amino-4-((4-chlorophenyl)thio)-bicyclo[3.1.0]hexane-2,6-dicarboxylic acid (a) 1SR,4RS,5SR,6SR-Ethyl-2-oxo-4-((4-chlorophenyl)thio)bicyclo[3.1.0]hexane-6-carboxylate Following the method of Example 1(b), but employing 2.19 g (13.2 mmol) of the product of Example 1(a) and 1.91 g, (13.2 mmol) 4-chlorothiophenol, followed by trituration from hexane afforded 3.76 g (91%) of the title compound FDMS: $M^+$=310, 312. Anal. Calcd. for $C_{15}H_{15}ClO_3S \cdot 0.1$ hexane: C, 58.67; H, 5.18; S, 10.03. Found: C, 58.77; H, 5.07; S, 9.60.

(b) 1SR,2RS,4SR,5SR,6SR-Ethyl-2-spiro-5'-hydantoin-4-((4-chlorophenyl)thio)-bicyclo[3.1.0]hexane-6-carboxylate Following the method of Example 1(c), but employing the product of step (a) (3.6 g, 11.6 mmol), $(NH_4)_2CO_3$ (4.5 g, 57.9 mmol) and KCN (1.5 g, 23.2 mmol), followed by filtering the product and recrystallization from EtOH yielded 1.9 g (43%) of the title compound. mp=256–258° C. FDMS: $M^+$=380. Anal. calcd. for $C_{17}H_{17}ClN_2O_4S \cdot 0.2\ H_2O$: C, 53.11; H, 4.56; N, 7.29; S, 8.34. Found: C, 52.90; H, 4.51; N, 7.12; S, 8.06.

(c) Following the method of Example 1(d), but employing the product of step (b) (0.60 g, 1.6 mmol) and 2N NaOH (15 mL) at reflux for 16 hours, work up afforded 0.045 g (9%) of the title compound. mp>250° C. FDMS: $M^+$=327 and 329. Anal. calcd. for $C_{14}H_{14}ClNO_4S \cdot 0.7\ H_2O$: C, 49.40; H, 4.56; N, 4.11; S, 9.42. Found: C, 49.11; H, 4.35; N, 4.49; S, 8.55.

EXAMPLE 5

1SR,2RS,4SR,5SR,6SR-2-Amino-4-(phenylsulfinyl) bicyclo[3.1.0]hexane-2,6-dicarboxylic acid (a) 1SR,2RS,4SR,5SR,6SR-Diethyl-2-aminoacetyl-4-(phenylthio)-bicyclo[3.1.0]hexane-2,6-dicarboxylate. A suspension of the product of Example 1 (1.0 g, 3.4 mmol) in EtOH (100 mL) was treated at 0° C. with $SOCl_2$ (2.0 g, 17.0 mmol) and then brought to reflux temperature for 30 h. The reaction mixture was concentrated to dryness under reduced pressure, the residue was dissolved in $CH_2Cl_2$ and, at 0° C., $iPr_2NEt$ (2.2 g, 17.0 mmol) and AcCl (0.8 g, 10.2 mmol) were added. After the reaction had proceeded at ambient temperature for 3 h, the mixtured was partitioned between $Et_2O$ and 1 N HCl and the organic phase was dried ($MgSO_4$). The mixture was subjected to chromatography (50% hexanes/EtOAc) affording 0.97 g (73%) of the title compound. FDMS: $M^+$=391. Anal. calcd. for $C_{20}H_{25}NO_5S$: C, 61.36; H, 6.44; N, 3.58; S, 8.19. Found: C, 61.16; H, 6.48; N, 3.33; S, 7.91.

(b) 1SR,2RS,4SR,5SR,6SR-Diethyl-2-aminoacetyl-4-(phenylsulfinyl)-bicyclo[3.1.0]hexane-2,6-dicarboxylate. A solution of m-CPBA (0.36 g, 1.2 mmol) in $CH_2Cl_2$ (20 mL) was added dropwise to a –78° C. solution of the product of step (a) (0.45 g, 1.2 mmol) in $CH_2Cl_2$ (50 mL), and the resulting reaction mixture stirred at –78° C. for 2 hours. The reaction was quenched with aqueous sodium thiosulfite, and partitioned between EtOAc and $H_2O$. The product was extracted with EtOAc, dried over $MgSO_4$ and concentrated to an oil which was purified by chromatography (50% EtOAc/hexanes to 67% EtOAc/hexanes) to afford 0.45 g (92%) of the title compound. FDMS: $M^+$+1=408. Anal. calcd. for $C_{20}H_{25}NO_6S$: C, 58.95; H, 6.18; N, 3.44; S, 7.87. Found: C, 58.65; H, 6.32; N, 3.21; S, 7.87.

(c) A solution of the product of step (c) (0.50 g, 1.2 mmol) in 5N HCl (25 mL) was warmed under reflux overnight. The reaction mixture was concentrated to dryness and then reconstituted in $H_2O$. The product was applied at pH=2 to Dowex® 50X8-100 cation exchange resin and eluted with 5% pyridine/$H_2O$ to afford 0.18 g (48%) of the title compound mp>250° C. FDMS: $M^+$=310. Anal. calcd. for $C_{14}H_{15}NO_5S \cdot 0.5\ H_2O$: C, 52.82; H, 5.02; N, 4.40; S, 10.07. Found: C, 52.60; H, 5.05; N, 4.72; S, 9.45.

EXAMPLE 6

1SR,2RS,4SR,5SR,6SR-2-Amino-4-(phenylsulfonyl)-bicyclo[3.1.0]hexane-2,6-dicarboxylic acid (a) 1SR,2RS,4SR,5SR,6SR-Diethyl-2-aminoacetyl-4-(phenylsulfonyl)-bicyclo[3.1.0]hexane-2,6-dicarboxylate . A solution of m-CPBA (0.45 g, 1.4 mmol) in $CH_2Cl_2$ (10 mL) was added dropwise to a 5° C. solution of the product of Example 5 (a) (0.45 g, 1.2 mmol) in $CH_2Cl_2$ (20 mL), and the resulting reaction mixture allowed to warm to ambient temperature as it stirred overnight. The reaction was partitioned between $CH_2Cl_2$ and 1N NaOH. The product was extracted with $CH_2Cl_2$, dried over $K_2CO_3$ and concentrated to yield 0.47 g (92%) of the title compound. mp=75–78° C. FDMS: $M^+$+1=424. Anal. calcd. for $C_{20}H_{25}NO_7S$: C, 56.73; H, 5.95; N, 3.31; S, 7.57. Found: C, 56.95; H, 6.21; N, 3.29; S, 7.29.

(b) The title compound was prepared by the method of Example 5(c), but employing the product of step (a) (0.36 g, 0.85 mmol) and 5N HCl (25 mL). The reaction mixture was concentrated to dryness and reconstituted in $H_2O$. The product was applied at pH=2 to Dowex® 50X8-100 cation exchange resin and eluted with 5% pyridine/$H_2O$ to afford 0.12 g (43%) of the title compound. mp>250° C. FDMS: $M^+$=326. Anal. calcd. for $C_{14}H_{15}NO_6S \cdot 0.25\ H_2O$: C, 50.98; H, 4.74; N, 4.25; S, 9.72. Found: C, 50.69; H, 4.61; N, 4.25; S, 9.72.

EXAMPLE 7

1SR,2RS,4SR,5SR,6SR-2-amino-4-((2-methoxyphenyl)thio)-bicyclo[3.1.0]hexane-2,6-dicarboxylic acid (a) 1SR,4RS,5SR,6SR-Ethyl-2-oxo-4-((2-methoxyphenyl)thio)-bicyclo[3.1.0]hexane-6-carboxylate.

Following the method of Example 1(b), but employing 2.0 g (12 mmol) of the product of Example 1(a) and 1.68 g (12 mmol) 2-methoxythiophenol, followed by crystallization from petroleum ether/ether afforded 2.73 g (74%) of the title compound. mp=102–104° C. FDMS: M$^+$=306. Anal. calcd. for $C_{16}H_{18}O_4S$: C, 62.72; H, 5.92; S, 10.46. Found: C, 63.00; H, 6.00; S, 10.61.

(b) 1SR,2RS,4SR,5SR,6SR-Diethyl-2-amino-4-((2-methoxyphenyl)thio)-bicyclo[3.1.0]hexane-2,6-dicarboxylate. Following the method of Example 8(b), but employing the product of step (a) (2.60 g, 8.49 mmol), $(NH_4)_2CO_3$ (2.00 g, 25.5 mmol) and KCN (0.83 g, 12.7 mmol) followed by hydrolysis with NaOH (2.40 g, 60.0 mmol) and esterification with $SOCl_2$ (10.0 g, 85 mmol) and purification by HPLC (10% EtOAc/hexanes to 75% EtOAc/hexanes) yielded 1.45 g (45%) of the title compound. FDMS: M$^+$=379. Anal. calcd. for $C_{19}H_{25}NO_5S\cdot 0.5\ H_2O$: C, 58.74; H, 6.75; N, 3.61; S, 7.23. Found: C, 58.86; H, 6.67; N, 3.77; S, 7.54.

(c) The product of step (b) (0.50 g, 1.30 mmol) was stirred in a 1:1 solution of 1N NaOH and THF (20 mL total volume) at ambient temperature overnight. The resulting reaction mixture was reduced under vacuum and reconstituted in $H_2O$. The product was applied at pH=10 to Bio-Rad AG® 1-X8 anion exchange resin and eluted with 50% acetic acid to afford the product as a white solid. Vacuum drying at 80° C. afforded 0.37 g (88%) of the title compound. mp=dec>250° C. FDMS: M$^+$=323. Anal. calcd. for $C_{15}H_{17}NO_5S$: C, 55.71; H, 5.30; N, 4.33; S, 9.92. Found: C, 55.42; H, 5.21; N, 4.48; S, 9.69.

EXAMPLE 8

1SR,2RS,4RS,5SR,6SR-2-Amino-4-((2-furanylmethyl)thio)bicyclo[3.1.0]hexane-2,6-dicarboxylic acid (a) 1SR,4RS,5SR,6SR-Ethyl-2-oxo-4-((2-furanylmethyl)thio)-bicyclo[3.1.0]hexane-6-carboxylate Following the method of Example 1(b), but employing 2.0 g (12 mmol) of the product of Example 1(a) and 1.37 g (12 mmol) 2-furanylmethylthiol, followed by purification by HPLC (10% EtOAc/hexanes to 50% EtOAc/hexanes) afforded 3.27 g (97%) of the title compound. FDMS: M$^+$=280. Anal. calcd. for $C_{14}H_{16}O_4S$: C, 59.98; H, 5.75; S, 11.44. Found: C, 59.97; H, 5.97; S, 10.25.

(b) 1SR,2RS,4RS,5SR,6SR-Diethyl-2-amino-4-((2-furanyl(methyl)thio)-bicyclo[3.1.0]hexane-2,6-dicarboxylate. The title compound was prepared by first subjecting the product of step (a) (3.14 g, 11.2 mmol) sequentially to the methods of Examples 1(c) [employing $(NH_4)_2CO_3$ (2.03 g, 26 mmol) and KCN (0.85 g, 13 mmol)] and 1(d) [employing 1M NaOH]. Th pH of the reaction mixture was adjusted to 1 with aqueous HCl and concentrated to dryness. The crude amino diacid hydrochloride was suspended in punctilious EtOH (200 mL) and chilled to 0° C. $SOCl_2$ (13.3 g, 112 mmol) was added dropwise to the suspension and the resulting reaction mixture warmed under reflux for 24 hours. The reaction mixture was concentrated to dryness and the resulting solids partitioned between 10% $NaHCO_3$/EtOAc. The product was extracted with EtOAc. All of the organic phases were combined, washed with brine, dried over $K_2CO_3$, and concentrated to an oil which was purified by HPLC (10% EtOAc/hexanes to 90% EtOAc/hexanes) affording the title compound (0.46 g, 1.30 mmol) 12%. FDMS: M$^+$=353. Anal. calcd. for $C_{17}H_{23}NO_5S\cdot 0.25\ H_2O$: C, 57.04; H, 6.62; N, 3.91; S, 8.96. Found: C, 57.22; H, 6.26; N, 3.69; S, 8.56.

(c) Following the method of Example 7(c), but employing the product of step (b) (0.25 g, 0.71 mmol). Anion exchange chromatography afforded 0.21 g (100%) of the title compound. mp>150° C. (dec). FDMS: M$^+$+1=298. Anal. calcd. for $C_{13}H_{15}NO_5S\cdot 0.8\ H_2O$: C, 50.09; H, 5.36; N, 4.49; S, 10.29. Found: C, 49.74; H, 4.96; N, 4.31; S, 9.44.

EXAMPLE 9

1SR,2RS,4SR,5SR,6SR-2-Amino-4-((2-methylphenyl)thio)bicyclo[3.1.0]hexane-2,6-dicarboxylic acid (a) 1SR,4RS,5SR,6SR-Ethyl-2-oxo-4-((2-methylphenyl)thio)-bicyclo[3.1.0]hexane-6-carboxylate Following the method of Example 1(b), but employing 3.3 g (20 mmol) of the product of Example 1(a) and 2.48 g (20 mmol) o-thiocresol. Crystallization from hexanes/EtOAc afforded 5.00 g (86%) of the title compound. mp=99–101° C. FDMS: M$^+$=290. Anal. calcd. for $C_{16}H_{18}O_3S$: C, 66.18; H, 6.25; S, 11.04. Found: C, 65.90; H, 6.27; S, 10.78.

(b) 1SR,2RS,4SR,5SR,6SR-Diethyl-2-amino-4-((2-methylphenyl)thio)-bicyclo[3.1.0]hexane-2,6-dicarboxylate Following the method of Example 8(b), but employing the product of step (a) (4.80 g, 16.5 mmol), $(NH_4)_2CO_3$ (3.87 g, 49.6 mmol) and KCN (1.61 g, 24.8 mmol); hydrolysis with NaOH (4.00 g, 100.0 mmol) and esterification with $SOCl_2$ (19.60 g, 165.0 mmol). Purification by HPLC (10% EtOAc/hexanes to 75% EtOAc/hexanes) yielded 2.95 g (49%) of the title compound. FDMS: M$^+$=363. Anal. calcd. for $C_{19}H_{25}NO_4S$: C, 62.79; H, 6.93; N, 3.85; S, 8.82. Found: C, 62.52; H, 6.84; N, 4.00; S, 8.91.

(c) The title compound was prepared by the method of Example 7(c), but employing the product of step (b) (0.75 g, 2.06 mmol). The product was isolated by precipitation at pH=3 affording 0.54 g (86%) of the title compound. mp=>250° C. FDMS: M$^+$=307. Anal. calcd. for $C_{15}H_{17}NO_4S$: C, 58.62; H, 5.57; N, 4.56; S, . Found: C, 58.66; H, 5.51; N, 4.36.

EXAMPLE 10

1SR,2RS,4SR,5SR,6SR-2-Amino-4-((3-fluorophenyl)thio)-bicyclo[3.1.0]hexane-2,6-dicarboxylic acid (a) 1SR,4RS,5SR,6SR-Ethyl-2-oxo-4-((3-fluorophenyl)thio)-bicyclo[3.1.0]hexane-6-carboxylate. Following the method of Example 1(b), but employing 3.3 g (20 mmol) of the product of Example 1(a) and 2.56 g (20 mmol) 3-fluorothiophenol, followed by crystallization from petroleum ether afforded 5.16 g (88%) of the title compound. mp=59–61° C. FDMS: M$^+$=294. Anal. calcd. for $C_{15}H_{15}FO_3S$: C, 61.21; H, 5.14; S, 10.89. Found: C, 61.23; H, 5.26; S, 10.99.

(b) 1SR,2RS,4SR,5SR,6SR-Diethyl-2-amino-4-((3-fluorobenzene)thio)-bicyclo[3.1.0]hexane-2,6-dicarboxylate. Following the method of Example 8(b), but employing the product of step (a) (5.00 g, 17.0 mmol), $(NH_4)_2CO_3$ (4.00 g, 51.0 mmol) and KCN (1.66 g, 25.5 mmol); followed by hydrolysis with NaOH (4.00 g, 100.0 mmol), esterification with $SOCl_2$ (20.2 g, 170 mmol), and purification by HPLC (10% EtOAc/hexanes to 75% EtOAc/hexanes) yielded 1.81 g (29%) of the title compound. FDMS: M$^+$=367. Anal. calcd. for $C_{18}H_{22}FNO_4S\cdot 0.2$ mole $H_2O$: C, 58.27; H, 6.09; N, 3.77; S, 8.64. Found: C, 58.17; H, 5.97; N, 3.96; S, 8.31.

(c) Following the method of Example 7(c), but employing the product of step (b) (0.25 g, 0.68 mmol), followed by precipitation at pH=3 afforded 0.18 g (85%) of the title compound mp>225° C. (dec). FDMS: M$^+$=311. Anal. calcd. for C$_{14}$H$_{14}$FNO$_4$S: C, 54.01; H, 4.53; N, 4.50. Found: C, 53.87; H, 4.51; N, 4.71.

EXAMPLE 11

1SR,2RS,4SR,5SR,6SR-2-Amino-4-(benzylthio)-bicyclo[3.1.0]hexane-2,6-dicarboxylic acid (a) 1SR,4RS,5SR, 6SR-Ethyl-2-oxo-4-(benzylthio)-bicyclo[3.1.0]-hexane-6-carboxylate. Following the method of Example 1(b), but employing 2.0 g (12 mmol) of the product of Example 1(a) and 1.50 g (12 mmol) benzyl mercaptan, followed by crystallization from petroleum ether/ether afforded 2.27 g (65%) of the title compound. mp=78–80° C. FDMS: M$^+$=290. Anal. calcd. for C$_{16}$H$_{18}$O$_3$S: C, 66.18; H, 6.25; S, 11.04. Found: C, 66.23; H, 6.32; S, 10.78.

(b) 1SR,2RS,4SR,5SR,6SR-Diethyl-2-amino-4-(benzylthio)-bicyclo[3.1.0]hexane-2,6-dicarboxylate. Following the method of Example 8(b), but employing the product of step (a) (2.15 g, 7.4 mmol), (NH$_4$)$_2$CO$_3$ (1.16 g, 14.8 mmol) and KCN (0.72 g, 11.1 mmol); hydrolysis with NaOH (2.50 g, 62.4 mmol) and esterification with SOCl$_2$ (8.9 g, 74 mmol). Purification by HPLC (10% EtOAc/hexanes to 50% EtOAc/hexanes) yielded 0.43 g (16%) of the title compound FDMS: M$^+$=363. Anal. calcd. for C$_{19}$H$_{25}$NO$_4$S: C, 62.78; H, 6.93; N, 3.85; S, 8.82. Found: C, 62.49; H, 6.77; N, 3.80; S, 8.52.

(c) Following the method of Example 7(c), but employing the product of step (b) (0.31 g, 0.85 mmol), followed by precipitation at pH=3 afforded 0.22 g (85%) of the title compound mp>250° C. (dec). FDMS: M$^+$=307. Anal. calcd. for C$_{15}$H$_{17}$NO$_4$S: C, 58.62; H, 5.57; N, 4.56. Found: C, 58.79; H, 5.50; N, 4.47.

EXAMPLE 12

1SR,2RS,4SR,5SR,6SR-2-Amino-4-((2-fluorophenyl)thio)-bicyclo[3.1.0]hexane-2,6-dicarboxylic acid (a) 1SR,4RS,5SR,6SR-Ethyl-2-oxo-4-((2-fluorophenyl)thio)-bicyclo[3.1.0]hexane-6-carboxylate Following the method of Example 1(b), but employing 3.3 g (20 mmol) of the produce of Example 1(a) and 2.56 g (20 mmol) 2-fluorothiophenol, followed by crystallization from petroleum ether afforded 5.20 g (88%) of the title compound mp=63–66° C. FDMS: M$^+$=294. Anal. calcd. for C$_{15}$H$_{15}$FO$_3$S: C, 61.21; H, 5.14; S, 10.89. Found: C, 61.41; H, 5.18; S, 10.92.

(b) 1SR,2RS,4SR,5SR,6SR-Diethyl-2-amino-4-((2-fluorobenzene)thio)-bicyclo[3.1.0]hexane-2,6-dicarboxylate Following the method of Exampole 8(b), but employing the product of step(a) (5.00 g, 17.0 mmol), (NH$_4$)$_2$CO$_3$ (4.00 g, 51.0 mmol) and KCN (1.66 g, 25.5 mmol); followed by hydrolysis with NaOH (4.00 g, 100.0 mmol), esterification with SOCl$_2$ (20.2 g, 170 mmol) and purification by HPLC (10% EtOAc/hexanes to 75% EtOAc/hexanes) yielded 1.63 g (26%) of the title compound. FDMS: M$^+$=367. Anal. calcd. for C$_{18}$H$_{22}$FNO$_4$S.0.25EtOAc: C, 58.60; H, 6.21; N, 3.60; S, 8.23. Found: C, 58.70; H, 6.08; N, 3.93; S, 8.15.

(c) Following the method of Example 7(c), but employing the product of step (b) (0.25 g, 0.68 mmol) followed by precipitation at pH=3 afford 0.24 g (112%) of the title compound. mp>250° C. FDMS: M$^+$+1=312. Anal. calcd. for C$_{14}$H$_{14}$NO$_4$S-0.70H$_2$O: C, 51.91; H, 4.79; N, 4.32. Found: C, 51.49; H, 4.19; N, 5.20.

EXAMPLE 13

1SR,2RS,4SR,5SR,6SR-2-Amino-4-((4-methylphenyl)thio)-bicyclo[3.1.0]hexane-2,6-dicarboxylic acid (a) 1SR,4RS,5SR,6SR-Ethyl-2-oxo-4-((4-methylphenyl)thio)-bicyclo[3.1.0]hexane-6-carboxylate. Following the method of Example 1(b), but employing 2.0 g (12 mmol) of the product of Example 1(a) and 1.50 g (12 mmol) p-thiocresol, followed by crystallization from petroleum ether/ether afforded 1.85 g (53%) of the title compound mp=84–86° C. FDMS: M$^+$=290. Anal. calcd. for C$_{16}$H$_{18}$O$_3$S: C, 66.18; H, 6.25; S, 11.04. Found: C, 65.90; H, 6.24; S, 10.97.

(b) 1SR,2RS,4SR,5SR,6SR-Diethyl-2-amino-4-((4-methylbenzene)thio)-bicyclo[3.1.0]hexane-2,6-dicarboxylate Following the method of Example 8(b), but employing the product of step (a) (2.55 g, 8.78 mmol), (NH$_4$)$_2$CO$_3$ (2.06 g, 26.3 mmol) and KCN (0.86 g, 13.2 mmol); followed by hydrolysis with NaOH (2.00 g, 50.0 mmol), esterification with SOCl$_2$ (10.47 g, 87.8 mmol), and purification by HPLC (10% EtOAc/hexanes to 75% EtOAc/hexanes) yielded 1.65 g (52%) of the title compound. FDMS: M$^+$=363. Anal. calcd. for C$_{19}$H$_{25}$NO$_4$S: C, 62.79; H, 6.93; N, 3.85; S, 8.82. Found: C, 62.81; H, 6.81; N, 4.01; S, 8.90.

(c) Following the method of Example 7(c), but employing the product of step (b) (0.25 g, 0.69 mmol), and isolate the product precipitation at pH=3 afforded 0.20 g (94%) of the title compound mp>240° C. (dec). FDMS: M$^+$=. Anal. calcd. for C$_{15}$H$_{17}$NO$_4$S: C, 58.62; H, 5.57; N, 4.56. Found: C, 58.64; H, 5.51; N, 4.30.

EXAMPLE 14

1SR,2SR,4SR,5RS,6SR-2-Amino-4-methylbicyclo[3.1.0]-hexane-2,6-dicarboxylic acid (a) (1SR,4SR,5RS,6SR)-Ethyl-2-oxo-4-methylbicyclo[3.1.0] hexane-6-carboxylate. Methyl lithium (1.6M) in diethyl ether was added to a slurry of copper (I) iodide (1.25 mmol) in anhydrous diethyl ether (6 ml) at 0° C. The solution was stirred for 30 min. at 0° and then 1SR,5RS,6SR-ethyl-2-oxobicyclo[3.1.0]hex-3-ene-6-carboxylate (0.84 mmol) in diethyl ether (2ml) was added dropwise. The mixture was then stirred for another hour at 0° C. and then it was quenched with saturated ammonium chloride solution and extracted with diethyl ether. The combined organic phases were dried over MgSO$_4$, filtered, and evaporated to dryness. Purification of the crude product by flash chromatography (hexane/ethyl acetate 4:1) gave the title compound as a colorless oil. Yield: 76%. $^1$H NMR (CDCL$_3$), δ: 4.1(q,2H,CH$_2$), 2.5(m,1H,H4), 2.35–2.19(m,3H,H1,H3d, H5), 2.1(t,1H,H6), 1.65(d,1H,H3u), 1.19 (t,3H,CH$_3$), 1.10 (d,3H,CH$_3$). $^{13}$C NMR (CDCL$_3$), δ: 211.13, 170.16, 61.13, 40.45, 36.09, 34.96, 29.93, 26.92, 21.80, 14.03. IR (KBr): 2961, 1731, 1270, 1186 cm$^{-1}$. Anal. Calcd for C$_{10}$H$_{14}$O$_3$: C, 65.91; H, 7.74. Found: C, 65.39; H, 7.60.

b) Mixture of (1SR,2SR,4SR,5RS,6SR)- and (1SR,2RS,4SR,5RS,6SR)-ethyl-2-amino-2-cyano-4-methylbicyclo[3.1.0] hexane-6-carboxylates. A heterogeneous mixture of alumina (14 g, Merck, Type 90 for column chromatography, neutral, activity I) and ammonium chloride (26 mmol) in acetonitrile (50 ml) was ultrasonically irradiated for 30 min.

Then, a solution of the product of step (a) (2.19 mmol) in acetonitrile (5 ml) was added and, after sonication for 2 additional hours 2.19 mmol of KCN was added. The mixture was sonicated overnight and then the alumina was filtered off and the filtrate was concentrated to dryness to give the title mixture of diastereomeric aminonitriles. This mixture was used in the next step without further purification.

c) (1SR,2SR,4SR,5RS,6SR) Ethyl-2-acetamido-2-cyano-4-methylbicyclo[3.1.0] hexane-6-carboxylate. To a solution of the produce of step (b) (1.25 mmol) in dry $CH_2Cl_2$ at 0° C., was added ethyl diisopropylamine (1.37 mmol) and the resultant mixture was stirred for 15 min. Then, acetyl chloride (1.37 mmol) was added and, after this mixture was stirred at ambient temperature for 5 h, it was quenched with water and extracted with $CH_2Cl_2$. The combined organic extracts were dried over $MgSO_4$ and evaporated to give an oil. The resultant mixture of acetylated aminonitriles was separated by column chromatography (hexane/ethyl acetate 1:1), using 230–400 mesh silica gel (Merck). Yield: 30%. $^1H$ NMR ($CDCl_3$), δ: 6.15 (s,1H,NH), 4.1(q,2H,J=7.1 Hz, $CH_2CH_3$), 2.7(dd,1H,J=2.8 Hz,H1), 2.55(d,1H,J=15Hz, H3u), 2.45 (m,1H,H4), 2.15–1.95 (m,5H,$CH_3CO$,H6,H5), 1.55(dd,1H,J=7.8 Hz,J=15 Hz), 1.25 (m,6H). $^{13}C$ NMR ($CDCl_3$),δ: 171.16, 169.97, 121.09, 61.28, 55.05, 42.26, 34.94, 34.62, 34.29, 23.03, 22.04, 21.15, 14.25 IR (KBr): 3284, 2245, 1730, 1655 $cm^{-1}$.

d) A mixture of the product of step (c) (0.8 mmol) and 5N HCl solution (10 ml) was heated under reflux overnight. The resulting solution was evaporated to dryness yielding a white solid. The title compound was isolated as a zwitterion after ion exchange chromatography on Dowex 50x8 50–100 Mesh using pyridine-water 10% as eluent. mp:>300° C.; Yield:31%. $^1H$ NMR ($D_2O$,Pyr), δ: 2.2 (dd,1H,J=3.1 Hz), 1.94(m,1H), 1.8–1.6 (m,3H), 1.52(t,1H), 0.9(d,3H,). $^{13}C$ NMR ($D_2O$),Pyr),δ: 176.86, 173.31, 64.90, 37.34, 32.26, 30.15, 23.13, 17.24. IR (KBr): 3428, 3234, 3103, 1676 $cm^{-1}$.

EXAMPLE 15

1SR,2SR,4SR,5RS,6SR-2-Amino-4-phenylbicyclo [3.1.0]hexane-2,6-dicarboxylic acid a) (1SR,4SR,5RS,6SR)-Ethyl-2-oxo-4-phenylbicyclo [3.1.0] hexane-6-carboxylate. Following the method of Example 14(a), but using phenyllithium (1.8m) in cyclohexane ether (12.5 mmol), the title compound was prepared. Yield: 70%. $^1H$ NMR ($CDCl_3$), δ: 7.11–7.4 (m,5H,Ph), 4.15(q,2H,$CH_2$), 3.60 (d,1H,H4), 2.65–2.48(m,3H,H1,H3d, H5), 2.2(t,1H,H6), 2.10(d,1H,H3u), 1.25(t,3H,$CH_3$). $^{13}C$ NMR($CDCl_3$), δ: 210.76, 170.11, 140.45, 129.15, 127.28, 126.58, 61.58, 40.94, 40.56, 35.89, 35.85, 26.88, 14.28. IR (KBr): 3063, 3130, 1739, 1270, 1186 $cm^{-1}$.

b) Mixture of (1SR,2SR,4SR,5RS,6SR)- and (1SR,2RS, 4RS,5RS,6SR)-ethyl-2-amino-2-cyano-4-phenylbicyclo [3.1.0]-hexane-6-carboxylate. Following the method of Example 14(b), but using the product of step (a), the title mixture of diastereoisomeric aminonitriles was prepared. This mixture was used in the next step without further purification.

c) (1SR,2SR,4RS,5RS,6SR) Ethyl-2-acetamido-2-cyano-4-phenylbicyclo[3.1.0]hexane-6-carboxylate. Following the method of Example 14(c), but using the product of step (b), the title compound was prepared. Yield: 20%. $^1H$ NMR ($CDCl_3$), δ: 7.4–7.2(m,5H,Ph), 6.35(s,1H,NH), 4.2(q, 2H,J= 7.2 Hz,$CH_2CH_3$), 3.65(d,1H,J=8.4 Hz,H4), 2.9(dd, 1H J=2.8 Hz, J=6.1 Hz, H1), 2.85 (d,1H,J=15.0 Hz, H3u), 2.4 (dd, 1H, J=3.3 Hz, J=6.1 Hz, H5), 2.0 (s,3H,$CH_3$), 1.9 (dd, 1H, J=8.4 Hz, J=15.0 Hz, H3d), 178(t, 1H, J=3.3 Hz), 1.29 (t, 3H, J=7.2 Hz, $CH_3$). $^{13}C$ NMR ($CDCl_3$), δ: 170.89, 170.34, 142.25, 128.56, 127.12, 127.06, 119.66, 61.20, 55.08, 44.84, 43.22, 35.68, 32.59, 22.66, 22.01, 14.06 IR (KBr): 3317, 2260, 1727, 1880, 1299, 1184 $cm^{-1}$.

d) Following the method of Example 14(d), but using the product of step (c), the title compound was prepared on a white solid. Yield: 67% $^1H$ NMR ($D_2O$,Pyr), δ: 7.05–6.8(m, 5H,Ph), 2.95(d,1H J=8.2 Hz, H4) 2.29(dd, 1H, J=3.0 Hz, J=6.1 Hz, H1), 2.1(d, 1H, J=14.3Hz, H3u), 1.7(dd,1H,J=2.8 Hz, J=6.1,H5), 1.52(m,1H,H3d), 1.45(t,1H, J=2.8 Hz,H6). $^{13}C$ NMR ($D_2O$, Pyr), δ: 180.95, 180.30, 144.11, 126.77, 125.87, 124.38, 65.27, 44.07, 42.77, 34.97, 31.07, 24.32. IR (KBr): 3445, 3196 $cm^{-1}$.

EXAMPLE 16

(1SR,2SR,4SR,5RS,6SR)-2-Amino-4-benzylbicyclo [3.1.0]hexane-2,6-dicarboxylic acid a) (1SR,4SR,5RS,6SR)-Ethyl-2-oxo-4-benzylbicyclo [3.1.0] hexane-6-carboxylate. Benzylmagnesium chloride (1M) in diethyl ether (24 mmol) was added dropwise to a stirred slurry of $CuBr.S(CH_3)_2$ (12 mmol) in anhydrous diethyl ether (14 ml) at −30° C. The mixture is stirred for 15 min. and then a mixture of 1SR,5RS,6SR-ethyl-2-oxobicyclo[3.1.0] hexane-6-carboxylate (4.8 mmol) and trimethyl silyl chloride (9.6 mmol) in anhydrous THF (7 ml) was slowly added. The solution was vigorously stirred at −30° C. for 30 min. and then it was quenched with a saturated ammonium chloride solution and extracted with diethyl ether. The combined extracts were dried over $MgSO_4$ and evaporated to dryness to give an oil which was purified by column chromatography (hexane/ethyl acetate 4:1) to give the title compound as a colorless oil. Yield: 50%. $^1H$ NMR ($CDCl_3$), δ: 7.39–7.15(m,5H,Ph), 4.10(q, 2H,$CH_2$), 2.80–2.61(m,3H), 2.4(m, 1H), 2.30(m,1H), 2.15(dd, 1H), 2.05(t,1H), 1.85(d,1H), 1.2(t3H). $^{13}C$ NMR ($CDCl_3$), δ: 210.87, 170.22, 138.45, 129.10, 128.63, 126.58, 61.33, 41.95, 38.48, 37.01, 35.13, 34.04, 26.86, 14.12.

b) Mixture of (1SR,2SR,4SR,5RS,6SR)- and (1SR,2RS, 4RS,5RS,6SR)-ethyl-2-amino-2-cyano-4-benzylbicyclo [3.1.0]-hexane-6-carboxylates. Following the method of Example 14(b), but using the product of step (a), the title mixture of diastereoisomeric aminonitriles was prepared. This mixture was used in the next step without further purification.

c) (1SR,2SR,4SR,5RS,6SR) Ethyl-2-acetamido-2-cyano-4-benzylbicyclo[3.1.0]hexane-6-carboxylate. Following the method of Example 14(c), but using the product of step (b), the title compound was prepared. Yield: 20%. $^1H$ NMR ($CDCl_3$), δ: 7.35–7.20(m,5H,Ph), 6.69(s,1H,NH), 4.1(q, 2H,$CH_2CH_3$), 2.90(m,2H), 2.80(dd, 1H J=3.0 Hz, J=6.2 Hz, H1), 2.55(m2H), 2.05(dd,1H), 1.90(s, 3H, $CH_3CO$), 1.65(t, 1H), 1.45 (dd,1H,J=7.9Hz,J=14.9 Hz, H3d), 1.23(t,3H, $CH_3CH_2$). $^{13}C$ NMR ($CDCl_3$), δ: 171.25, 170.39, 139.29, 129.21, 128.77, 126.59, 120.87, 61.30, 54.88, 42.20, 40.83, 39.16, 34.48, 32.50, 22.93, 21.88, 14.22 IR (KBr): 3316, 2240, 1726, 1659, 1294, 1185 $cm^{-1}$.

d) Following the method of Example 14(d), but using the product of step (c), the title compound was prepared as a white solid. Yield: 47%. $^1H$ NMR ($D_2O$,Pyr), δ: 7.30–7.05 (m,5H,Ph), 2.93(d,2H,J=7.9Hz), 2.65(m,1H), 2.3(m,1H), 2.29–2.15(m,2H), 1.9(m,1H), 1.8(dd,1H,J=8.4 Hz,J=14.7 Hz). $^{13}C$ NMR ($D_2O$,Pyr),δ: 178.00, 174.00, 139.57, 127.87, 126.98, 124.41, 64.58, 39.91, 36.77, 34.23, 30.31, 30.17, 22.87. IR (KBr): 3419,3123,1684 $cm^{-1}$.

EXAMPLE 17

1SR,2SR,4SR,5RS,6SR-2-Amino-4-(4-fluorophenyl)-bicyclo[3.1.0]hexane-2,6-dicarboxylic acid a) (1SR,4SR,5RS,6SR)-Ethyl-2-oxo-4-(4-fluorophenyl)-bicyclo[3.1.0]hexane-6-carboxylate. Following the method of Example 16(a) but using p-fluorophenylmagnesium bromide (1M) in THF (24 mmol), the title compound was prepared. Yield: 50%. $^1$H NMR (CDCl$_3$), δ: 7.05–6.80 (m,4H,Ph), 4.00(q,2H,CH$_2$), 3.48(d,1H,H4), 2.50–2.35(m, 3H,H1,H3d,H5), 2.08(t,1H,H6), 1.95(d,1H,H3u), 1.1(t,3H, CH$_3$). $^{13}$C NMR (CDCl$_3$), δ: 210.70, 169.86, 159.81, 140.07. 140.03, 127.99, 127.87, 116.15–115.54, 61.49, 41.07, 39.85, 35.60, 26.69, 14.08. Anal. Calcd for C$_{15}$H$_{15}$O3F: C, 68.68; H, 5.76. Found: C, 68.44; H, 5.72.

b) Mixture of (1SR,2SR,4SR,5RS,6SR) and (1SR,2RS, 4SR, 5RS,6SR)-ethyl-2-amino-2-cyano-4-(4-fluorophenyl) bicyclo [3.1.0]hexane-6-carboxylates. Following the method of Example 14(b), but using the product of step (a), the title mixture of diastereomeric aminonitriles was prepared. This mixture was used in the next step without further purification.

c) (1SR,2SR,4RS,5RS,6SR)-Ethyl-2-acetamido-2-cyano-4-(4-fluorophenyl)bicyclo[3.1.0]hexane-6-carboxylate. Following the method of Example 14(c), but using the product of step (b), the title compound was prepared. Yield: 30%. $^1$H NMR (CDCl$_3$), δ: 7.38–7.30(m,2H, Ph), 7.1(t,2H,Ph), 6.35 (s,1H,NH), 4.15(q,2H,CH$_2$CH$_3$), 3.6(d,1H,J=8.5 Hz,H4), 2.98(dd,1H,J=2.8 Hz,J=6.09 Hz,H1), 2.81(d,1H,J=15.0 Hz,H3u), 2.38(dd,1H, J=3.3Hz, J=6.09 Hz,H5), 2.0(s,3H, CH$_3$CO), 1.9(dd,1H,J=8.5 Hz, J=15.04,H6), 1.3(t,3H, CH$_3$CH$_2$). $^{13}$C NMR (CDCl$_3$), δ: 170.81, 170.11, 164.0, 138.10, 128.95, 115.80, 119.63, 61.51, 55.26, 44.53, 43.72, 35.81, 32.61, 22.98, 22.20, 14.27. IR (KBr): 3433, 2245, 1726, 1646 cm$^{-1}$.

d) Following the method of Example 14(d), but using the product of step (c) the title compound was prepared as a white solid. mp:>300° C.; Yield:42%. $^1$H NMR (D$_2$O,Pyr), δ: 7.1–6.9 (m,2H,Ar), 6.65(t,2H,Ar), 3.1(d,1H,J=6.9 Hz), 2.45 (m,1H), 2.25–1.95(m,3H), 1.7(m,1H). $^{13}$C NMR (D$_2$O, Pyr), δ: 181.99, 181.56, 162.86, 158.08, 140.94–140.88, 128.47–128.31, 114.47–114.05, 66.09, 44.04, 43.36, 35.67, 31.86, 24.97. IR (KBr): 3420, 3163, 2921, 1740, 1715 cm$^{-1}$.

EXAMPLE 18

1SR,2RS,4SR,5SR,6SR-2-Amino-4-(3-fluorophenylsulfinyl)-bicyclo[3.1.0]hexane-2,6-dicarboxylic acid (a) 1SR,2RS,4SR,5SR,6SR-Diethyl-2-acetylamino-4-((3-fluorophenyl)thio)-bicyclo[3.1.0]hexane-2,6-dicarboxylate. A solution of the product of Example 10(b) (1.38 g, 3.76 mmol) in CH$_2$Cl$_2$ (35 mL), at 0° C., was treated consecutively with diisopropylethylamine (1.46 g, 11.3 mmol), then acetyl chloride (0.59 g, 7.50 mmol). The resulting reaction mixture was allowed to warm to ambient temperature and stirred until the reaction was complete by TLC. The reaction mixture was partitioned between Et$_2$O and 1 N HCl and and the product extracted with Et$_2$O. All organic phases were combined, washed with brine, and dried (MgSO$_4$). The mixture was subjected to chromatography (10% EtOAc/hexanes to 50% EtOAc/hexanes) affording 1.41 g (3.44 mmol, 92%) of the title compound. FDMS: M$^+$=409. Anal. calcd. for C$_{20}$H$_{24}$FNO$_5$S-0.5 H2O: C, 57.40; H, 6.02; N, 3.35; S, 7.66. Found: C, 57.29; H, 6.09; N, 3.25; S, 11.11.

(b) 1SR,2RS,4SR,5SR,6SR-Diethyl-2-acetylamino-4-((3-fluorophenyl)sulfinyl)-bicyclo[3.1.0]hexane-2,6-dicarboxylate. m-CPBA (0.24 g, 0.76 mmol) was added in one portion to a −78° C. solution of the product of step (a) (0.31 g, 0.76 mmol) in CH$_2$Cl$_2$ (20 mL), and the resulting reaction mixture stirred at −78° C. for 4 hours. The reaction mixture was partitioned between 1N NaOH and Et$_2$O. The product was extracted with Et$_2$O, dried over MgSO$_4$ and concentrated to an oil which was purified by PC-TLC chromatography (10% EtOAc/hexanes to 100% EtOAc) to afford 0.27 g (0.63 mmol, 84%) of the title compound. FDMS: M$^+$=425. Anal. calcd. for C$_{20}$H$_{24}$FNO$_6$S: C, 56.46; H, 5.69; N, 3.29; S, 7.54. Found: C, 56.70; H, 5.72; N, 3.41; S, 7.30.

(c) A solution of the product of step (b) (0.21 g, 0.49 mmol) in 2N HCl (25 mL) was warmed under reflux overnight. The reaction mixture was concentrated to dryness and then reconstituted in H$_2$O. The product was applied at pH=2 to Dowex® 50X8-100 cation exchange resin and eluted with 5% pyridine/H2O to afford 1.45 g (0.39 mmol, 76%) of the title compound. mp>250° C. (dec). FDMS: M$^+$+1=328. Anal. calcd. for C$_{14}$H$_{15}$NO$_5$S.1.1 H$_2$O: C, 48.44; H, 4.70; N, 4.03. Found: C, 48.15; H, 4.38; N, 3.98.

EXAMPLE 19

1SR,2RS,4SR,5SR,6SR-2-Amino-4-(2-methoxyphenylsulfonyl)-bicyclo[3.1.0]hexane-2,6-dicarboxylic acid (a) 1SR,2RS,4SR,5SR,6SR-Diethyl-2-aminoacetyl-4-((2-methoxyphenyl)thio)-bicyclo[3.1.0]hexane-2,6-dicarboxylate. Following the method of Example 18(a), but employing the product of Example 7(b) (0.60 g, 1.58 mmol), i-Pr$_2$Et (0.60 g, 4.5 mmol), and acetyl chloride (0.24 g, 3.0 mmol); followed by purification by HPLC (10% EtOAc/hexanes to 90% EtOAc/hexanes) afforded 0.58 g (1.38 mmol, 87%) of the title compound. FDMS: M$^+$=421. Anal. calcd. for C$_{21}$H$_{27}$NO$_6$S-0.2 H2O: C, 59.33; H, 6.50; N, 3.29; S, 7.54. Found: C, 59.69; H, 6.72; N, 3.44; S, 7.24.

(b) 1SR,2RS,4SR,5SR,6SR-Diethyl-2-aminoacetyl-4-((2-methoxyphenyl)sulfonyl)-bicyclo[3.1.0]hexane-2,6-dicarboxylate. The product of step (a) (0.48 g, 1.14 mmol) and m-CPBA (0.78 g, 2.5 mmol) were combined in CH2Cl2 (30 mL) at 0° C. and the reaction mixture was allowed to warm to room temperature with stirring overnight. The reaction mixture was partitioned between 1N NaOH and Et2O, the product was extracted with Et2O, washed with brine, and dried over MgSO4. After concentration to dryness, the product was purified by PC-TLC (10% EtOAc/hexanes to 67% EtOAc/hexanes) to afford 0.44 g (0.97 mmol, 85%) of the title compound. FDMS: M$^+$+1=454. Anal. calcd. for C$_{21}$H$_{27}$NO$_8$S-0.25 H2O: C, 55.07; H, 6.05; N, 3.06; S, 7.00. Found: C, 55.12; H, 6.09; N, 2.91; S, 6.82.

(c) A solution of the product of step (b) (0.36 g, 0.79 mmol) in 2N HCl (25 mL) was warmed under reflux for 72 h. The reaction mixture was concentrated to dryness and then reconstituted in H2O. The pH was adjusted to 14 by addition of NaOH, and the solids were filtered and discarded. The pH of the filtrate was adjusted to 3 by addition of 3 N HCl, and the precipitated product was isolated by filtration followed by drying under vacuum at 80° C. overnight yielding 0.17 g (0.48 mmol, 61%) of the title compound. mp>270° C. FDMS: M$^+$+1=356. Anal. calcd. for C$_{15}$H$_{17}$NO$_7$S-0.25 H2O: C, 50.06; H, 4.90; N, 3.89. Found: C, 50.06; H, 4.79; N, 3.93.

EXAMPLE 20

1SR,2RS,4SR,5SR,6SR-2-Amino-4-(2-fluorophenylsulfinyl)-bicyclo[3.1.0]hexane-2,6-dicarboxylic acid (a) 1SR,2RS,4SR,5SR,6SR-Diethyl-2-aminoacetyl-4-((2-fluorophenyl)thio)-bicyclo[3.1.0]hexane-2,6-dicarboxylate.

Following the method of Example 18(b), but employing the product of Example 12(c) (1.25 g, 3.44 mmol), iPr2NEt (1.33 g, 10.3 mmol), and acetyl chloride (0.41 g, 5.16 mmol); followed by purification by HPLC (10% EtOAc/hexanes to 90% EtOAc/hexanes) afforded 1.17 g (2.86 mmol, 92%) of the title compound. FDMS: M$^+$=409. Anal. calcd. for $C_{20}H_{24}FNO_5S$: C, 58.67; H, 5.91; N, 3.42; S, 7.83. Found: C, 58.40; H, 6.01; N, 3.22; S, 7.55.

(b) 1SR,2RS,4SR,5SR,6SR-Diethyl-2-aminoacetyl-4-((2-fluorophenyl)sulfinyl)-bicyclo[3.1.0]hexane-2,6-dicarboxylate. Following the method of Example 18(b), but employing the product of step (a) (0.30 g, 0.73 mmol) and m-CPBA (0.28 g, 0.88 mmol); followed by purification by PC-TLC (10% EtOAc/hexanes to 67% EtOAc/hexanes) to afford 0.24 g (0.56 mmol, 77%) of the title compound. FDMS: M$^+$=425. Anal. calcd. for $C_{20}H_{24}FNO_6S$: C, 56.46; H, 5.69; N, 3.29; S, 7.54. Found: C, 56.27; H, 5.67; N, 3.06; S, 7.44.

(c) The title compound was prepared following the method of Example 19(c), but employing the product of step (b) (0.16 g, 0.38 mmol) and 2N HCl (25 mL); followed by precipitation of the product from solution (pH=3) afforded 0.08 g (0.24 mmol, 64%) of the title compound. mp>250° C. (dec). FDMS: M$^+$+1=328. Anal. calcd. for $C_{14}H_{15}NO_5S.0.5 H_2O$: C, 50.00; H, 4.50; N, 4.16. Found: C, 49.80; H, 4.23; N, 4.05.

EXAMPLE 21

1SR,2RS,4SR,5SR,6SR-2-Amino-4-(2-fluorophenylsulfonyl)-bicyclo[3.1.0]hexane-2,6-dicarboxylic acid (a) 1SR,2RS,4SR,5SR,6SR-Diethyl-2-aminoacetyl-4-((2-fluorophenyl)sulfonyl)-bicyclo[3.1.0]hexane-2,6-dicarboxylate. Following the method of Example 19(b), but employing the product of 20(a) (0.79 g, 1.93 mmol) and m-CPBA (1.33 g, 4.24 mmol); followed by purification by PC-TLC (50% EtOAc/hexanes to 100% EtOAc) to afford 0.73 g (1.66 mmol, 86%) of the title compound. FDMS: M$^+$+1=442. Anal. calcd. for $C_{20}H_{24}FNO_7S$: C, 64.41; H, 5.48; N, 3.17; S, 7.26. Found: C, 64.29; H, 5.64; N, 3.18; S, 7.02.

(b) The title compound was prepared following the method of Example 19(c), but employing the product of step (a) (0.60 g, 1.36 mmol) and 2N HCl (25 mL); followed by precipitation of the product at pH=3 afforded 0.37 g (1.10 mmol,79%) of the title compound. mp>275° C. FDMS: M$^+$+1=344. Anal. calcd. for $C_{14}H_{14}FNO_6S$: C, 48.98; H, 4.11; N, 4.08. Found: C, 48.70; H, 4.15; N, 4.01.

EXAMPLE 22

1SR,2RS,4SR,5SR,6SR-2-Amino-4-(2-methylphenylsulfonyl)-bicyclo[3.1.0]hexane-2,6-dicarboxylic acid (a) 1SR,2RS,4SR,5SR,6SR-Diethyl-2-aminoacetyl-4-((2-methylphenyl)thio)-bicyclo[3.1.0]hexane-2,6-dicarboxylate. Following the method of Example 18(a), but employing the product of Example 9(b) (2.0 g, 5.5 mmol), iPr2NEt (2.13 g, 16.5 mmol), and acetyl chloride (0.66 g, 8.3 mmol); followed by purification by HPLC (10% EtOAc/hexanes to 50% EtOAc/hexanes) afforded 2.06 g (5.1 mmol, 92%) of the title compound. FDMS: M$^+$=405. Anal. calcd. for $C_{21}H_{27}NO_5S$: C, 62.20; H, 6.71; N, 3.45; S, 7.91. Found: C, 62.48; H, 7.01; N, 3.53; S, 7.57.

(b) 1SR,2RS, 4SR,5SR,6SR-Diethyl-2-aminoacetyl-4-((2-methylphenyl)sulfonyl)-bicyclo[3.1.0]hexane-2,6-dicarboxylate. Following the method of Example 19(b), but employing the product of step (a) (1.14 g, 2.81 mmol) and m-CPBA (2.21 g, 7.0 mmol); followed by purification by prep HPLC (10% EtOAc/hexanes to 50% EtOAc/hexanes) afforded 1.20 g (2.74 mmol, 98%) of the title compound. FDMS: M$^+$=437. Anal. calcd. for $C_{21}H_{27}NO_7S$: C, 57.65; H, 6.22; N, 3.20; S, 7.33. Found: C, 57.54; H, 6.23; N, 3.14; S, 7.06.

(c) The title compound was prepared following the method of Example 19(c), but employing the product of step (b) (1.05 g, 2.4 mmol) and 2N HCl (30 mL); follwed by precipitation of the product at pH 3 afforded 0.71 g (2.1 mmol, 88%) of the title compound. mp>275° C. FDMS: M$^+$+1=340. Anal. calcd. for $C_{15}H_{17}NO_6S$: C, 53.09; H, 5.05; N, 4.13. Found: C, 53.21; H, 5.12; N, 4.17.

EXAMPLE 23

1SR,2RS,4SR,5SR,6SR-2-Amino-4-(4-methylphenylsulfonyl)-bicyclo[3.1.0]hexane-2,6-dicarboxylic acid (a) 1SR,2RS,4SR,5SR,6SR-Diethyl-2-aminoacetyl-4-((4-methylphenyl)thio)-bicyclo[3.1.0]hexane-2,6-dicarboxylate. Following the method of Example 18(a), but employing the product of Example 13(b) (1.25 g, 3.44 mmol), iPr2NEt (1.33 g, 10.3 mmol), and acetyl chloride (0.41 g, 5.16 mmol); followed by purification by prep HPLC (10% EtOAc/hexanes to 90% EtOAc/hexanes) affording 1.37 g (3.38 mmol, 98%) of the title compound. FDMS: M$^+$=405. Anal. calcd. for $C_{21}H_{27}NO_5S$: C, 62.20; H, 6.71; N, 3.45; S, 7.91. Found: C, 62.20; H, 6.90; N, 3.34; S, 8.02.

(b) 1SR,2RS,4SR,5SR,6SR-Diethyl-2-aminoacetyl-4-((4-methylphenyl)sulfonyl)-bicyclo[3.1.0]hexane-2,6-dicarboxylate. Following the method of Example 19(b), but employing the product of step (a) (0.86 g, 2.12 mmol) and m-CPBA (1.66 g, 5.3 mmol); followed by purification by prep HPLC (10% EtOAc/hexanes to 50% EtOAc/hexanes) to afford 0.90 g (2.06 mmol, 97%) of the title compound. FDMS: M$^+$=437. Anal. calcd. for $C_{21}H_{27}NO_7S$: C, 57.65; H, 6.22; N, 3.20; S, 7.33. Found: C, 57.54; H, 6.37; N, 3.22; S, 7.15.

(c) The title compound was prepared following the method of Example 19(c), but employing the product of step (b) (0.76 g, 1.74 mmol) and 2N HCl (30 mL); followed by precipitation of the product at pH=3 afforded 0.71 g (2.1 mmol, 88%) of the title compound. mp>270° C. FDMS: M$^+$+1=340. Anal. calcd. for $C_{15}H_{17}NO_6S$: C, 53.09; H, 5.05; N, 4.13. Found: C, 53.00; H, 4.94; N, 4.07.

EXAMPLE 24

1SR,2RS,4SR,5SR,6SR-2-Amino-4-((3-methylphenyl)thio)bicyclo[3.1.0]hexane-2,6-dicarboxylic acid (a) 1SR,4RS,5SR,6SR-Ethyl-2-oxo-4-((3-methylphenyl)thio)-bicyclo[3.1.0]hexane-6-carboxylate. Following the method of Example 1(b), but employing 3.32 g (20 mmol) of the product of Example 1(a) and 2.48 g (20 mmol) m-thiocresol. Trituration with petroleum ether afforded 5.25 g (18.1 mmol, 90%) of the title compound. mp=63–65° C. FDMS: M$^+$=290. Anal. calcd. for $C_{16}H_{18}O_3S$: C, 66.18; H, 6.25; S, 11.04. Found: C, 65.94; H, 6.28; S, 11.24.

(b) 1SR,2RS,4SR,5SR,6SR-Diethyl-2-amino-4-((3-methylphenyl)thio)-bicyclo[3.1.0]hexane-2,6-dicarboxylate. Following the method of Example 8(b), but employing the product of step (a) (4.30 g, 14.8 mmol), ($NH_4)_2CO_3$ (3.47 g, 44.4 mmol) and KCN (1.45 g, 22.2 mmol); hydrolysis with NaOH (4.00 g, 100.0 mmol) and esterification with $SOCl_2$ (17.60 g, 148.0 mmol). Purification by HPLC (10% EtOAc/hexanes to 90% EtOAc/hexanes) yielded 2.41 g (45%) of the title compound. FDMS: $M^+$=363. Anal. calcd. for $C_{19}H_{25}NO_4S$-0.25 $H_2O$: C, 62.02; H, 6.99; N, 3.81; S, 8.71. Found: C, 62.11; H, 6.85; N, 3.75; S, 8.49.

(c) The title compound was prepared by the method of Example 7(c), but employing the product of step (b) (1.20 g, 3.30 mmol). The product was isolated by precipitation at pH=3 affording 0.90 g (2.9 mmol, 89%) of the title compound. mp>250° C. FDMS: $M^+$=307. Anal. calcd. for $C_{15}H_{17}NO_4S$: C, 58.62; H, 5.57; N, 4.56; S, 10.43. Found: C, 58.45; H, 5.38; N, 4.76; S, 10.42.

EXAMPLE 25

1SR,2RS,4SR,5SR,6SR-2-Amino-4-(2-phenylethylthio) bicyclo[3.1.0]hexane-2,6-dicarboxylic acid (a) 1SR,4RS,5SR,6SR-Ethyl-2-oxo-4-(2-phenylethylthio)-bicyclo[3.1.0]hexane-6-carboxylate. Following the method of Example 1(b), but employing 3.32 g (20 mmol) of the product of Example 1(a) and 3.03 g (22.2 mmol) phenethyl mercaptan. Crystallization from hexanes/EtOAc afforded 3.86 g (12.7 mmol, 63%) of the title compound. mp=53–55° C. FDMS: $M^+$=304. Anal. calcd. for $C_{17}H_{20}O_3S$: C, 67.08; H, 6.62; S, 10.53. Found: C, 67.33; H, 6.49; S, 11.08.

(b) 1SR,2RS,4SR,5SR,6SR-Diethyl-2-amino-4-(2-phenylethylthio)-bicyclo[3.1.0]hexane-2,6-dicarboxylate. Following the method of Example 8(b), but employing the product of step (a) (3.70 g, 12.2 mmol), $(NH_4)_2CO_3$ (2.85 g, 36.5 mmol) and KCN (1.19 g, 18.3 mmol); hydrolysis with NaOH (5.00 g, 125.0 mmol) and esterification with $SOCl_2$ (14.52 g, 132.0 mmol). Purification by HPLC (10% EtOAc/hexanes to 90% EtOAc/hexanes) yielded 1.09 g (2.90 mmol, 24%) of the title compound. FDMS: $M^+$=377. Anal. calcd. for $C_{19}H_{25}NO_4S$-0.5 H2O: C, 62.15; H, 7.30; N, 3.62; S, 8.30. Found: C, 62.41; H, 6.95; N, 3.45; S, 7.85.

(c) The title compound was prepared by the method of Example 7(c), but employing the product of step (b) (0.54 g, 1.68 mmol). The product was isolated by precipitation at pH=3 affording 0.42 g (1.3 mmol, 78%) of the title compound. mp>275° C. FDMS: $M^+$=321. Anal. calcd. for $C_{16}H_{19}NO_4S$: C, 59.79; H, 5.96; N, 4.36; S, 9.98. Found: C, 60.03; H, 6.04; N, 4.50; S, 9.94.

EXAMPLE 26

1SR,2RS,4SR,5SR,6SR-2-Amino-4-(2-phenylethylsulfonyl)-bicyclo[3.1.0]hexane-2,6-dicarboxylic acid (a) 1SR,2RS,4SR,5SR,6SR-Diethyl-2-aminoacetyl-4-(2-phenylethylthio)-bicyclo[3.1.0]hexane-2,6-dicarboxylate. Following the method of Example 18(a), but employing the product of Example 25(b) (0.32 g, 0.85 mmol), iPr2NEt (0.22 g, 1.7 mmol), and acetyl chloride (0.10 g, 1.3 mmol); followed by purification by PC-TLC (10% EtOAc/hexanes to 50% EtOAc/hexanes) affording 0.26 g (0.62 mmol, 73%) of the title compound. FDMS: $M^+$=419. Anal. calcd. for $C_{21}H_{27}NO_5S$-1.0 H2O: C, 60.39; H, 7.14; N, 3.20; S, 7.33. Found: C, 60.28; H, 6.80; N, 3.25; S, 7.14.

(b) The title compound was prepared in two steps from the product of step (a), by sequentially following the methods of 19(b), [employing the product of step (a) (0.12 g, 0.29 mmol) and m-CPBA (0.22 g, 0.73 mmol)] and 19(c). Isolation of the product by preciptation at pH=3 afforded 0.04 g (0.12 mmol, 40%) of the title compound. mp>245° C. (dec). FDMS: $M^+$+1=354. Anal. calcd. for $C_{16}H_{19}NO_6S$: C, 54.38; H, 5.42; N, 3.96; S, 9.07. Found: C, 54.13; H, 5.52; N, 3.99; S, 8.92.

EXAMPLE 27

1SR,2RS,4SR,5SR,6SR-2-Amino-4-(2-phenylpropylthio) bicyclo[3.1.0]hexane-2,6-dicarboxylic acid (a) 1SR,4RS,5SR,6SR-Ethyl-2-oxo-4-(2-phenylpropylthio)-bicyclo[3.1.0]hexane-6-carboxylate. Following the method of Example 1(b), but employing 3.32 g (20 mmol) of the product of Example 1(a) and 3.34 g (22.2 mmol) phenpropyl mercaptan. Crystallization from petroleum ether/Et2O afforded 4.36 g (13.7 mmol, 68%) of the title compound. mp=60–62° C. FDMS: $M^+$=318. Anal. calcd. for $C_{18}H_{22}O_3S$: C, 67.89; H, 6.96; S, 10.07. Found: C, 67.77; H, 7.14; S, 10.42.

(b) 1SR,2RS,4SR,5SR,6SR-Diethyl-2-amino-4-(2-phenylpropylthio)-bicyclo[3.1.0]hexane-2,6-dicarboxylate. Following the method of Example 8(b), but employing the product of step (a) (4.20 g, 13.2 mmol), $(NH_4)_2CO_3$ (3.12 g, 39.6 mmol) and KCN (1.30 g, 19.8 mmol); hydrolysis with NaOH (5.00 g, 125.0 mmol) and esterification with $SOCl_2$ (15.70 g, 132.0 mmol). Purification by prep HPLC (10% EtOAc/hexanes to 90% EtOAc/hexanes) yielded 0.76 g (1.90 mmol, 15%) of the title compound. FDMS: $M^+$=391. Anal. calcd. for $C_{21}H_{29}NO_4S$-0.25 H2O: C, 63.69; H, 7.51; N, 3.54; S, 8.10. Found: C, 63.73; H, 7.49; N, 3.77; S, 8.15.

(c) The title compound was prepared following the method of Example 7(c), but employing the product of step (b) (0.27 g, 0.69 mmol). The product was isolated by precipitation at pH=3 affording 0.21 g (0.63 mmol, 91%) of the title compound. mp>260° C. (dec.). FDMS: $M^+$=335. Anal. calcd. for $C_{17}H_{21}NO_4S$: C, 60.87; H, 6.31; N, 4.18; S, 9.56. Found: C, 60.84; H, 6.18; N, 4.47; S, 9.59.

EXAMPLE 28

1SR,2RS,4SR,5SR,6SR-2-Amino-4-((3-methoxyphenyl)thio) bicyclo[3.1.0]hexane-2,6-dicarboxylic acid (a) 1SR,4RS,5SR,6SR-Ethyl-2-oxo-4-((3-methoxyphenyl)thio)-bicyclo[3.1.0]hexane-6-carboxylate. Following the method of Example 1(b), but employing 3.32 g (20 mmol) of the product of Example 1(a) and 2.80 g (20 mmol) 3-methoxybenzenethiol. Trituration with petroleum ether afforded 5.30 g (17.3 mmol, 87%) of the title compound. mp=54–57° C. FDMS: $M^+$=306. Anal. calcd. for $C_{16}H_{18}O_4S$: C, 62.72; H, 5.92; S, 10.46. Found: C, 62.96; H, 5.96; S, 10.48.

(b) 1SR,2RS,4SR,5SR,6SR-Diethyl-2-amino-4-((3-methoxyphenyl)thio)-bicyclo[3.1.0]hexane-2,6-dicarboxylate. Following the method of Example 8(b), but employing the product of step (a) (5.15 g, 16.8 mmol), $(NH_4)_2CO_3$ (3.93 g, 50.4 mmol) and KCN (1.64 g, 25.2 mmol); hydrolysis with NaOH (4.00 g, 100.0 mmol) and esterification with $SOCl_2$ (20.0 g, 168.0 mmol). Purification by HPLC (10% EtOAc/hexanes to 25% EtOAc/hexanes) yielded 0.97 g (2.56 mmol, 15%) of the title compound. FDMS: $M^+$+1=380. Anal. calcd. for $C_{19}H_{25}NO_5S$-0.33 $H_2O$: C, 59.21; H, 6.71; N, 3.63; S, 8.32. Found: C, 59.31; H, 6.47; N, 4.17; S, 7.75.

(c) The title compound was prepared following the method of Example 7(c), but employing the product of step (b) (0.50 g, 1.32 mmol). The product was isolated by precipitation at pH=3 affording 0.31 g (1.25 mmol, 95%) of the title compound. mp>270° C. FDMS: M+=323. Anal. calcd. for $C_{15}H_{17}NO_5S$: C, 55.71; H, 5.30; N, 4.33; S, 9.91. Found: C, 55.64; H, 5.14; N, 4.38; S, 9.82.

EXAMPLE 29

1SR,2SR,4RS,5RS,6SR-2-Amino-4-phenylbicyclo [3.1.0]hexane-2,6-dicarboxylic acid (a) 1SR,5RS,6SR-Ethyl-4-phenyl-2-oxobicyclo[3.1.0] hex-3-ene-carboxylate. Iodotrimethylsilane (5 g, 25 mmol) was added dropwise to a 0° solution of ethyl-4-phenyl-2-oxobicyclo-[3.1.0]hexane-6-carboxylate (prepared as described in Example 15(a)) (4.37 mmol) and triethylamine (26.5 mmol) in anhydrous $CH_2Cl_2$ (18 ml). The resulting reaction mixture was allowed to warm to ambient temperature and stirred for six hours. The reaction mixture was washed with aqueous $NaHCO_3$ and brine, dried over $MgSO_4$ and concentrated in vacuo. The resulting oil was percolated through a short column of silicagel (EtOAc/Hexane 1:4) to give an oil which was used without further purification. The product was reconstituted in anhydrous $CH_3CN$ (50 ml) and treated in one portion with $Pd(AcO)_2$ (1.1 g, 4.9 mmol), and stirred at ambient temperature for 1 hour. The reaction mixture was diluted with ether and filtered through a pad of Celite. The filtrate was concentrated in vacuo to give the crude product which was purified by flash chromatography ($CH_2Cl_2$). Yield: 54%. $^1$H NMR ($CDCl_3$), δ:7.65 (m, 2H), 7.47 (m, 3H), 5.99 (S, 1H), 4.17 (m, 2H), 3.27 (m, 1H), 2.71 (m, 1H), 2.37 (m, 1H), 1.22 (m, 3H) ppm $^{13}$C NMR ($CDCl_3$), δ: 202.5, 171.1, 168.5, 131.7, 129.2, 127.0, 121.4, 61.6, 58.6, 43.9, 31.2, 28.6, 14.2 ppm.

(b) 1SR,4RS,5RS,6SR-Ethyl-2-oxo-4-phenylbicyclo-[3.1.0]-hexane-6-carboxylate. To a solution of the product of step (a) (2.31 mmol) in EtOH (150 ml) was added 110 mg of Pd on charcoal (10%). The reaction was allowed to proceed under hydrogen (20 psi) at room temperature for 45 minutes. Filtration of the catalyst through Celite gave the title compound whose purification was achieved by flash chromatography (Hexane/Ethyl Acetate 4:1). Yield: 76%. $^1$H NMR ($CDCl_3$), δ: 7.39–7.24 (m, 2H), 7.28–7.24 (m, 3H), 4.14 (m, 2H), 3.89 (m, 1H), 2.84 (m, 1H), 2.55 (m, 1H), 2.42 (m, 1H), 2.20 (m, 1H), 2.13 (m, 1H), 1.24 (m, 3H) ppm $^{13}$C NMR ($CDCl_3$), δ:209.3, 170.2, 140.7, 128.8, 127.0, 126.8, 61.4, 39.1, 38.3, 36.3, 32.7, 24.8, 14.1 ppm. Anal. Calcd for $C_{15}H_{16}O_3$: C, 73.75; H, 6.60. Found: C, 73.66; H, 6.27.

(c) Mixture of 1SR,2SR,4SR,5RS,6SR and 1SR,2RS, 4SR,5RS,6SR-ethyl-2-amino-2-cyano-4-phenylbicyclo-[3.1.0]hexane-6-carboxylates. Following the method of Example 14(b) but using the product of step (b), the title mixture of diastereoisomeric aminonitriles was prepared. This mixture was used without further purification.

(d) 1SR,2SR,4SR,5RS,6SR-Ethyl-2-acetamido-2-cyano-4-phenylbicyclo[3.1.0]hexane-6-carboxylate. Following the method of Example 14 (c), but using the product of step (c), the title compound was prepared. Yield: 34%. $^1$H NMR ($CDCl_3$), δ: 7.37–7.23 (m, 5H), 6.28 (s, 1H), 4.14 (q, 2H), 3.91 (m, 1H), 3.11 (m, 1H), 2.76 (m, 1H), 2.42 (m, 1H), 1.96 (m, 1H), 1.41 (m, 1H), 1.27 (t, 3H) ppm $^{13}$C NMR ($CDCl_3$), δ: 171.1, 170.6, 139.3, 128.6, 127.1, 126.7, 119.4, 61.2, 55.5, 42.0, 39.5, 32.6, 30.3, 22.7, 19.0, 14.0 ppm.

(e) Following the method of Example 14 (d), but using the product of step (d), the title compound was prepared as a white solid. Yield: 62%. $^1$H NMR ($D_2O$, KOD), δ: 7.95–7.84 (m, 5H), 4.27 (s, 1H), 2.87 (m, 1H), 2.65 (s, 1H), 2.56 (s, 1H), 2.26 (s, 1H), 1.73 (s, 1H) ppm.

EXAMPLE 30

1SR,2SR, 4RS, 5RS,6SR-2-Amino-4-benzylbicyclo [3.1.0]hexane-2,6-dicarboxylic acid (a) 1SR,5RS,6SR-Ethyl-4-benzyl-2-oxobicyclo[3.1.0] hex-3-ene-6-carboxylate. Following the method of Example 1(a), but using as starting material ethyl 4-benzyl-2-oxobicyclo-[3.1.0]hexane-6-carboxylate (prepared as described in Example 16(a)), the title compound was prepared. Yield: 48%. $^1$H NMR ($CDCl_3$), δ: 7.31–7.11 (m, 5H), 5.27 (s, 1H), 4.05 (q, 2H), 3.69 (m, 2H), 2.72 (m, 1H), 2.50 (m, 1H), 2.14 (m, 1H), 1.19 (t, 3H) ppm $^{13}$C NMR ($CDCl_3$), δ: 202.7, 177.1, 168.2, 136.3, 129.1, 129.0, 127.3, 124.6, 61.4, 44.7, 39.3, 31.3, 30.4, 14.2 ppm.

(b) 1SR,4RS,5RS,6SR-Ethyl-2-oxo-4-benzylbicyclo-[3.1.0]-hexane-6-carboxylate. Following the method of Example 1(b), but using the product of step (a), the title product was prepared. Yield: 82%. $^1$H NMR ($CDCl_3$), δ: 7.28, 7.10 (m, 5H), 4.12 (m, 2H), 2.75 (m, 3H), 2.33 (m, 1H), 2.26 (m, 1H), 2.09 (m, 2H), 1.71 (m, 1H), 1.23 (m, 3H), ppm $^{13}$C NMR ($CDCl_3$), δ: 210.0, 170.2, 138.9, 128.54, 128.50, 126.4, 61.2, 39.5, 38.0, 36.7, 36.6, 32.9, 23.9, 14.11 ppm.

(c) Mixture of 1SR 2SR,4RS,5RS,6SR and 1SR,2RS, 4RS,5RS,6SR-ethyl-2-amino-2-cyano-4-phenylbicyclo [3.1.0]hexane-6-carboxylates. Following the method of Example 14(b), but using the product of step (b), the title mixture of diastereoisomeric aminonitriles was prepared. This mixture was used without further purification.

(d) 1SR,2SR,4RS,5RS,6SR-Ethyl-2-acetamido-2-cyano-4-benzylbicyclo[3.1.0]hexane-6-carboxylate. Following the method of Example 14(c), but using the product of step (c), the title compound was prepared. Yield: 42%. $^1$H NMR ($CDCl_3$), δ: 7.27–7.16 (m, 3H), 7.12–7.09 (m, 2H), 6.9 (s, 1H), 4.09 (m, 2H), 2.86 (m, 1H), 2.65 (m, 3H), 2.02 (m, 1H), 1.97 (s, 3H), 1.75 (m, 1H), 1.19 (m, 4H), 1.05 (m, 1H) ppm $^{13}$C NMR ($CDCl_3$), δ: 171.1, 170.1, 139.1, 129.1, 126.5, 119.4, 61.1, 55.5, 39.8, 38.9, 38.2, 33.3, 30.6, 22.8, 18.3, 14.1 ppm.

(e) Following the method of Example 14(d), but using the product of step (d), the title compound was prepared as a white solid. Yield: 40%. $^1$H NMR ($D_2O$, KOD), δ: 7.96–7.82 (m, 5H), 3.31–3.16 (m, 3H), 2.47 (m, 2H), 2.18 (m, 2H), 1.47 (m, 1H) ppm. $^{13}$C NMR ($CDCl_3$), δ: 183.5, 182.7, 142.1, 129.3, 128.8, 126.2, 66.4, 41.7, 40.9, 39.0, 36.7, 32.0, 21.8 ppm.

We claim:

1. A compound of the formula

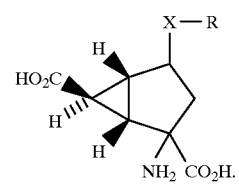

I in which X represents a bond, S, SO or $SO_2$; and R represents a (1-6C) alkyl group; a (2-6C)alkenyl group; a (2-6C)alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1-6C) alkyl, (2-6C)alkenyl or (2-6C)alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; or a non-toxic metabolically labile ester or amide thereof; or a pharmaceutically acceptable salt thereof.

2. A compound as claimed in claim 1, in which R represents 2-naphthyl; phenyl which is unsubstituted or substituted by one or two substituents selected independently from halogen, (1-4C)alkyl and (1-4C)alkoxy; a pyrimidyl group; a benzyl group or a 2-thiophenylmethyl group.

3. A compound as claimed in claim 1, in which R represents a (1-6C)alkyl group; a phenyl group which is unsubstituted or substituted by one or two substituents selected independently from halogen, (1-4C)alkyl and (1-4C)alkoxy; or a phenyl (1-4C)alkyl or diphenyl (1-4C) alkyl group which is unsubstituted or substituted on phenyl by one or two substituents selected from halogen, (1-4C) alkyl and (1-4C)alkoxy.

4. A compound as claimed in claim 1, in which R represents 2-naphthyl, phenyl, 2-fluorophenyl, 3-fluorophenyl, 4-fluorophenyl, 3,4-difluorophenyl, pentafluorophenyl, 2-chlorophenyl, 3-chlorophenyl, 4-chlorophenyl, 3,4-dichlorophenyl, 2,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 3-trifluoromethylphenyl or 4-trifluoromethylphenyl.

5. A compound as claimed in claim 1, which has the stereochemistry shown below.

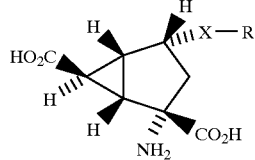

6. A compound as claimed in claim 1, in which X represents S.

7. A compound as claimed in claim 1, in which X represents a bond.

8. A process for the preparation of a compound of formula I which comprises (a) hydrolyzing a compound of formula

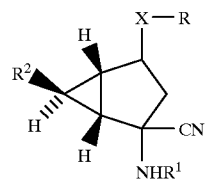

II in which $R^1$ represents a hydrogen atom or an acyl group and $R^2$ represents a carboxyl group or an esterified carboxyl group, or a salt thereof;

(b) hydrolyzing a compound of formula

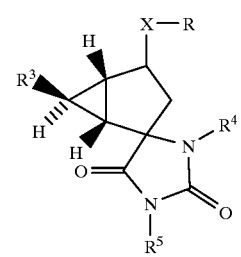

III in which $R^3$ represents a carboxyl group or an esterified carboxyl group, and $R^4$ and $R^5$ each independently represent a hydrogen atom, a (2-6C) alkanoyl group, a (1-4C) alkyl group, a (3-4C) alkenyl group or a phenyl (1-4C) alkyl group in which the phenyl is unsubstituted or substituted by halogen, (1-4C) alkyl or (1-4C) alkoxy, or a salt thereof; or (c) deprotecting a compound of formula

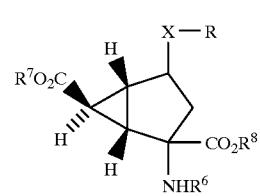

IV in which $R^6$ represents a hydrogen atom or a nitrogen protecting group and each of $R^7$ and $R^8$ independently represents a hydrogen atom or a carboxyl protecting group, or a salt thereof;

whereafter, if necessary and/or desired
(i) resolving the compound of formula I;
(ii) converting the compound of formula I into a non-toxic metabolically labile ester thereof; and/or;
(iii) converting the compound of formula I or a non-toxic metabolically labile ester thereof into a pharmaceutically acceptable salt thereof.

9. A pharmaceutical formulation, which comprises a compound as claimed in claim 1 and a pharmaceutically acceptable carrier, diluent or excipient.

10. A method of modulating one or more metabotropic glutamate receptor functions in a warm blooded mammal requiring such treatment, which comprises administering an effective amount of a compound as claimed in claim 1.

* * * * *